US012805996B2

(12) United States Patent
Greenhalgh et al.

(10) Patent No.: US 12,805,996 B2
(45) Date of Patent: Nov. 24, 2026

(54) COMPLIANCE CONTROL STITCHING IN SUBSTRATE MATERIALS

(71) Applicant: TELA Bio, Inc., Malvern, PA (US)

(72) Inventors: Skott Greenhalgh, Gladwyne, PA (US); John-Paul Romano, Chalfont, PA (US)

( * ) Notice: Subject to any disclaimer, the term of this patent is extended or adjusted under 35 U.S.C. 154(b) by 57 days.

(21) Appl. No.: 18/920,684

(22) Filed: Oct. 18, 2024

(65) Prior Publication Data

US 2025/0041040 A1 Feb. 6, 2025

Related U.S. Application Data

(63) Continuation of application No. 17/747,313, filed on May 18, 2022, now Pat. No. 12,144,714, which is a
(Continued)

(51) Int. Cl.
*A61F 2/00* (2006.01)
*A61L 31/00* (2006.01)
(Continued)

(52) U.S. Cl.
CPC .............. *A61F 2/0063* (2013.01); *A61F 2/00* (2013.01); *A61L 31/005* (2013.01); *A61L 31/048* (2013.01); *A61L 31/146* (2013.01); *D05B 93/00* (2013.01); *D05C 17/00* (2013.01); *A61F 2002/0068* (2013.01);
(Continued)

(58) Field of Classification Search
CPC .. A61F 2/0063; A61F 2/00; A61F 2002/0068; A61F 2210/0004; A61F 2210/0057; A61F 2210/0076; A61F 2250/0018; A61F 2250/0028; A61F 2250/0029; A61F 2250/003; A61L 31/005; A61L 31/048; A61L 31/146; A61L 2430/34; D05B 93/00; D05C 17/00
See application file for complete search history.

(56) References Cited

U.S. PATENT DOCUMENTS 2,259,025 A 10/1941 Cosgro
3,033,139 A 5/1962 Tateishi
(Continued)

FOREIGN PATENT DOCUMENTS

DE 10312674 A1 10/2003
DE 112007001732 T5 4/2011
(Continued)

OTHER PUBLICATIONS

Greenhalgh et al.; U.S. Appl. No. 19/009,833 entitled "Textured medical textiles," filed Jan. 3, 2025.
(Continued)

*Primary Examiner* — Richard G Louis

(57) ABSTRACT

Compliance control stitch patterns sewn or embroidered into biotextile or medical textile substrates impart reinforcing strength, and stretch resistance and control into such substrates. Compliance control stitch patterns may be customizable to particular patients, substrate implantation sites, particular degenerative or diseased conditions, or desired time frames. Substrates having compliance control stitch patterns sewn or embroidered into them may be used in tissue repair or tissue reconstruction applications.

16 Claims, 13 Drawing Sheets

Related U.S. Application Data continuation of application No. 16/554,329, filed on Aug. 28, 2019, now Pat. No. 11,369,464, which is a continuation of application No. 15/215,704, filed on Jul. 21, 2016, now Pat. No. 10,426,587.

(60) Provisional application No. 62/195,089, filed on Jul. 21, 2015.

(51) Int. Cl.

| | |
|---|---|
| ***A61L 31/04*** | (2006.01) |
| ***A61L 31/14*** | (2006.01) |
| ***D05B 93/00*** | (2006.01) |
| ***D05C 17/00*** | (2006.01) |

(52) U.S. Cl.

CPC ................. *A61F 2210/0004* (2013.01); *A61F 2210/0057* (2013.01); *A61F 2210/0076* (2013.01); *A61F 2250/0018* (2013.01); *A61F 2250/0028* (2013.01); *A61F 2250/0029* (2013.01); *A61F 2250/003* (2013.01); *A61L 2430/34* (2013.01)

(56) References Cited

U.S. PATENT DOCUMENTS 3,054,406 A 9/1962 Usher
3,155,095 A 11/1964 Brown
3,364,200 A 1/1968 Ashton et al.
3,658,023 A 4/1972 Rossi
4,466,370 A 8/1984 Eguchi et al.
5,593,441 A 1/1997 Lichtenstein et al.
5,634,931 A 6/1997 Kugel
5,683,400 A 11/1997 McGuire
5,707,395 A 1/1998 Li
5,723,010 A 3/1998 Yui et al.
5,919,232 A 7/1999 Chaffringeon et al.
5,990,378 A 11/1999 Ellis
6,120,539 A 9/2000 Eldridge et al.
6,258,124 B1 7/2001 Darois et al.
6,319,264 B1 11/2001 Törmälä et al.
6,371,985 B1 4/2002 Goldberg
6,383,201 B1 5/2002 Dong
6,652,595 B1 11/2003 Nicolo
6,814,748 B1 11/2004 Baker et al.
6,962,120 B1 11/2005 Fujikura et al.
7,824,420 B2 11/2010 Eldridge et al.
7,883,494 B2 2/2011 Martin
7,946,236 B2 5/2011 Butcher
8,074,591 B2 12/2011 Butcher et al.
8,182,545 B2 5/2012 Cherok et al.
8,236,342 B2 8/2012 Thomas et al.
8,853,294 B2 10/2014 Myung et al.
8,974,428 B2 3/2015 Freedman et al.
9,205,052 B2 12/2015 Kim et al.
9,289,279 B2 3/2016 Wilson et al.
9,295,757 B2 3/2016 Patel et al.
9,326,840 B2 5/2016 Mortarino
9,364,310 B2 6/2016 Stopek
9,421,079 B2 8/2016 Koullick et al.
9,468,705 B2 10/2016 Geller
9,510,925 B2 12/2016 Hotter et al.
9,554,887 B2 1/2017 Lecuivre
9,585,838 B2 3/2017 Hartounian et al.
9,770,414 B2 9/2017 Garcia et al.
9,775,700 B2 10/2017 Greenhalgh et al.
9,820,843 B2 11/2017 Greenhalgh et al.
9,925,030 B2 3/2018 Greenhalgh et al.
10,130,457 B2 11/2018 Greenhalgh et al.
10,213,284 B2 2/2019 Greenhalgh et al.
10,426,587 B2 10/2019 Greenhalgh et al.
10,500,030 B2 12/2019 Greenhalgh et al.
10,561,485 B2 2/2020 Greenhalgh et al.
10,675,141 B2 6/2020 Greenhalgh et al.
10,702,364 B2 7/2020 Greenhalgh et al.
11,344,397 B2 5/2022 Greenhalgh et al.
11,369,464 B2 6/2022 Greenhalgh et al.
11,426,156 B2 8/2022 Coleman et al.
11,446,130 B2 9/2022 Greenhalgh et al.
11,464,616 B2 10/2022 Greenhalgh et al.
11,590,262 B2 2/2023 Greenhalgh
11,628,054 B2 4/2023 Greenhalgh et al.
11,864,987 B2 1/2024 Greenhalgh et al.
12,016,972 B2 6/2024 Greenhalgh
12,064,334 B2 8/2024 Greenhalgh et al.
12,070,380 B2 8/2024 Greenhalgh et al.
12,144,714 B2 11/2024 Greenhalgh et al.
12,208,000 B2 1/2025 Greenhalgh et al.
2001/0020188 A1 9/2001 Sander
2002/0111392 A1 8/2002 Cruise
2003/0023316 A1 1/2003 Brown et al.
2003/0225355 A1 12/2003 Butler
2004/0010320 A1 1/2004 Huckle et al.
2004/0033212 A1 2/2004 Thomson et al.
2004/0054376 A1 3/2004 Ory et al.
2004/0078089 A1 4/2004 Ellis et al.
2004/0138762 A1 7/2004 Therin et al.
2004/0249457 A1 12/2004 Smith et al.
2005/0070930 A1* 3/2005 Kammerer ............ A61F 2/0063 606/151
2005/0113849 A1 5/2005 Popadiuk et al.
2005/0113938 A1 5/2005 Jamiolkowski et al.
2005/0118236 A1 6/2005 Qiu et al.
2005/0255543 A1 11/2005 Just et al.
2006/0178683 A1 8/2006 Shimoji et al.
2006/0217747 A1 9/2006 Ferree
2006/0229722 A1 10/2006 Bianchi et al.
2007/0088434 A1 4/2007 Frank
2007/0190108 A1 8/2007 Datta et al.
2007/0224238 A1 9/2007 Mansmann et al.
2007/0250147 A1 10/2007 Walther et al.
2008/0097601 A1 4/2008 Codori-Hurff et al.
2008/0167729 A1 7/2008 Nelson et al.
2008/0181928 A1 7/2008 Hakimi-Mehr et al.
2009/0018655 A1 1/2009 Brunelle et al.
2009/0054339 A1 2/2009 Marshall et al.
2009/0069893 A1 3/2009 Paukshto et al.
2009/0082864 A1 3/2009 Chen et al.
2009/0149939 A1 6/2009 Godlewski et al.
2009/0216338 A1 8/2009 Gingras et al.
2009/0306688 A1 12/2009 Patel et al.
2009/0326577 A1 12/2009 Johnson et al.
2010/0010114 A1 1/2010 Myung et al.
2010/0028396 A1* 2/2010 Ward .................... A61F 2/0059 623/23.72
2010/0063599 A1 3/2010 Brunelle et al.
2010/0100107 A1 4/2010 Duggal et al.
2010/0120679 A1 5/2010 Xu et al.
2010/0217388 A1 8/2010 Cohen et al.
2010/0249929 A1 9/2010 Kurz et al.
2010/0254900 A1 10/2010 Campbell et al.
2010/0305500 A1 12/2010 Lambert et al.
2010/0311949 A1 12/2010 Akkus et al.
2010/0318108 A1 12/2010 Datta et al.
2010/0318124 A1 12/2010 Leung et al.
2011/0014153 A1 1/2011 Derwin et al.
2011/0020420 A1 1/2011 Bosley et al.
2011/0125287 A1 5/2011 Hotter et al.
2011/0166673 A1* 7/2011 Patel .................. A61L 27/3625 623/23.72
2011/0196490 A1 8/2011 Gadikota et al.
2011/0250264 A1 10/2011 Schutt et al.
2011/0257761 A1 10/2011 Mortarino
2011/0301717 A1 12/2011 Becker
2012/0010637 A1 1/2012 Stopek et al.
2012/0035608 A1 2/2012 Marchitto et al.
2012/0082712 A1 4/2012 Stopek et al.
2012/0095482 A1 4/2012 Peterson et al.
2012/0143329 A1 6/2012 Kim
2012/0165957 A1 6/2012 Everland et al.
2012/0179176 A1 7/2012 Wilson et al.
2012/0184974 A1 7/2012 Becker
2012/0253464 A1 10/2012 Hwang et al.

(56) References Cited

U.S. PATENT DOCUMENTS

| | | | |
|---|---|---|---|
| 2013/0064772 | A1 | 3/2013 | Swiss et al. |
| 2013/0116799 | A1 | 5/2013 | Derwin et al. |
| 2013/0172994 | A1 | 7/2013 | Becker |
| 2013/0197300 | A1 | 8/2013 | Koullick et al. |
| 2013/0209547 | A1 | 8/2013 | Garcia et al. |
| 2013/0211307 | A1 | 8/2013 | Evans et al. |
| 2013/0267137 | A1 | 10/2013 | Peniston et al. |
| 2013/0303958 | A1 | 11/2013 | Holm et al. |
| 2013/0304098 | A1 | 11/2013 | Mortarino |
| 2013/0317286 | A1 | 11/2013 | Bluecher et al. |
| 2014/0090942 | A1 | 4/2014 | Schlipper |
| 2014/0094931 | A1 | 4/2014 | Derwin et al. |
| 2014/0182498 | A1 | 7/2014 | Torigoe |
| 2014/0276993 | A1 | 9/2014 | Reilly et al. |
| 2014/0364878 | A1 | 12/2014 | Ladet et al. |
| 2015/0112434 | A1 | 4/2015 | Felix et al. |
| 2015/0127103 | A1 | 5/2015 | Seedhom |
| 2015/0267330 | A1 | 9/2015 | Carrier et al. |
| 2015/0297798 | A1 | 10/2015 | Badylak et al. |
| 2016/0058534 | A1 | 3/2016 | Derwin et al. |
| 2016/0058589 | A1 | 3/2016 | Bar et al. |
| 2016/0136289 | A1 | 5/2016 | Puri et al. |
| 2016/0206580 | A1 | 7/2016 | Los et al. |
| 2016/0262208 | A1 | 9/2016 | Hsieh |
| 2016/0374791 | A1 | 12/2016 | Lecuivre et al. |
| 2017/0027679 | A1 | 2/2017 | Serban et al. |
| 2017/0086972 | A1 | 3/2017 | Braido et al. |
| 2017/0245847 | A1 | 8/2017 | Obermiller et al. |
| 2019/0008623 | A1 | 1/2019 | Nemoto et al. |
| 2019/0234937 | A1 | 8/2019 | Wang et al. |
| 2020/0360129 | A1 | 11/2020 | Moses et al. |
| 2021/0128793 | A1 | 5/2021 | Mongrain et al. |
| 2021/0290416 | A1 | 9/2021 | Hall et al. |
| 2021/0322666 | A1 | 10/2021 | Greener |
| 2022/0110749 | A1 | 4/2022 | Hariton et al. |
| 2022/0126013 | A1 | 4/2022 | Selby et al. |
| 2022/0211367 | A1 | 7/2022 | Schmid et al. |
| 2023/0008637 | A1 | 1/2023 | Greenhalgh et al. |
| 2023/0293281 | A1 | 9/2023 | Greenhalgh et al. |
| 2023/0338637 | A1 | 10/2023 | Nazerali et al. |
| 2024/0299628 | A1 | 9/2024 | Greenhalgh |
| 2024/0374367 | A1 | 11/2024 | Romano et al. |
| 2025/0090295 | A1 | 3/2025 | Greenhalgh et al. |
| 2025/0268701 | A1 | 8/2025 | Greenhalgh et al. |
| 2025/0387543 | A1 | 12/2025 | Greenhalgh |

FOREIGN PATENT DOCUMENTS

| | | | |
|---|---|---|---|
| EP | 2198854 | A2 | 6/2010 |
| EP | 2229918 | A1 | 9/2010 |
| EP | 2300066 | A2 | 3/2011 |
| EP | 2344133 | A2 | 7/2011 |
| JP | 2015025033 | A | 2/2015 |
| KR | 10-2007-0122546 | A | 12/2007 |
| RU | 2524196 | C2 | 7/2014 |
| WO | WO00/57812 | A1 | 10/2000 |
| WO | WO02/078568 | A1 | 10/2002 |
| WO | WO03/082363 | A1 | 10/2003 |
| WO | WO03/094781 | A1 | 11/2003 |
| WO | WO2008/095038 | A1 | 8/2008 |
| WO | WO2012/017415 | A2 | 2/2012 |
| WO | WO2012/138514 | A1 | 10/2012 |
| WO | WO2017/050837 | A1 | 3/2017 |
| WO | WO2017/191276 | A1 | 11/2017 |
| WO | WO2017/223462 | A1 | 12/2017 |

OTHER PUBLICATIONS

Deeken et al., Physiocomechanical evaluation of absorbable and nonabsorbable barrier composite meshes for laparoscopic ventral hernia repair. Surg. Endosc., 25(5), 1541-1552 ( 12 pages, Author Manuscript); May 2011.

Franklin et al.; Uptake of tetracycline by aortic aneurysm wall and its effect on inflammation and proteolysis; British Journal of Surgery; 86(6); pp. 771-775; Jun. 1999.

Mayo Clinic;Placement of Breast Implants; retrieved May 25, 2017 from http://www.mayoclinic.org/placement-of-breast-implants/img-20007384; 1 pg; May 25, 2017.

Pyo et al.; Targeted gene disruption of matrix metalloproteinase-9 (gelatinase B) suppresses development of experimental abdominal aortic aneurysms; The Journal of Clinical Investigation; 105(11); pp. 1641-1649; Jun. 2000.

Tambiah et al.; Provocation of experimental aortic inflammation and dilatation by inflammatory mediators and chlamydia pneumoniae; British Journal of Surgery; 88(7); pp. 935-940; Jul. 2001.

Walton et al.; Inhibition of prostoglandin E2 synthesis in abdominal aortic; Circulation; 100; pp. 48-54, 8 pages; Jul. 1999.

Xu et al.; Sp1 increases expression of cyclooxygenase-2 in hypoxic vascular endothelium implications for the mechanisms of aortic aneurysm and heart failure; journal of Biological Chemistry; 275(32); pp. 24583-24589; Aug. 2000.

Nazerali; U.S. Appl. No. 17/447,166 entitled "Subcutaneous and pocket irrigator," filed Sep. 8, 2021.

Greenhalgh et al.; U.S. Appl. No. 18/779,698 entitled "Layered materials for implants," filed Jul. 22, 2024.

* cited by examiner

COMPLIANCE CONTROL STITCHING IN SUBSTRATE MATERIALS

CROSS REFERENCE TO RELATED APPLICATIONS

This application is a continuation of U.S. patent application Ser. No. 17/747,313, filed May 18, 2022, titled "COMPLIANCE CONTROL STITCHING IN SUBSTRATE MATERIALS," now U.S. Patent Application Publication No. 2022/0273412, which is a continuation of U.S. patent application Ser. No. 16/554,329, filed on Aug. 28, 2019, titled "COMPLIANCE CONTROL STITCHING IN SUBSTRATE MATERIALS," now U.S. Pat. No. 11,369,464, which is a continuation of U.S. patent application Ser. No. 15/215,704, filed on Jul. 21, 2016, titled "COMPLIANCE CONTROL STITCHING IN SUBSTRATE MATERIALS," now U.S. Pat. No. 10,426,587, which claims priority to U.S. Provisional Application No. 62/195,089, filed on Jul. 21, 2015, titled "COMPLIANCE CONTROL STITCHING IN BIOLOGIC SUBSTRATE MATERIALS," the contents of each application are incorporated by reference herein, in their entirety and for all purposes.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The disclosure relates generally to the field of sewing. More particularly, the disclosure relates to compliance control stitch patterns sewn or embroidered into, for example, biotextile or medical textile substrates such as implants for soft tissue repair, regeneration, or reconstruction.

BACKGROUND

Various publications, including patents, patent applications, technical articles and scholarly articles are cited throughout the specification. Each of these cited publications is incorporated by reference herein, in its entirety and for all purposes.

The success of implanted surgical repair materials is highly variable. This variability is compounded when considering procedures where the repair material must support both an immediate post-operative biomechanical load, as in for example repair of abdominal wall hernia defects or other procedures (wherein replacement or strengthening of soft tissue is required or desired), and subsequently maintain the desired repair characteristics over the expected duration of the implant.

Some commonly available repair materials for hernial or other soft tissue defects include synthetic meshes and collagen based sheets of allogeneic or xenogeneic material. Each of these suffers from inherent limitations that may make them less than optimal for the full and immediate repair of such a defect. Synthetic meshes, while possessing good tensile characteristics, do not necessarily integrate with the patient's body and over time may become a source of adhesions as they are progressively infiltrated with or covered by scar tissue. Additionally, synthetic meshes are more prone to infection, which often leads to subsequent removal and replacement.

Collagen sheets, often derived from human or animal skin, pericardium, intestinal tissue or bladder or constructed from collagen suspensions, are often cross-linked to render them inert or minimally reactive to the patient's body and to provide some increased mechanical strength. This cross-linking process devitalizes the repair matrix, preventing proper infiltration, adherence and remodeling by the patient's cells and resulting in a similarly non-integrative material. A subset of implantable collagen matrices are those that are chemically processed to remove cellular and antigenic components and are often described as revitalizing tissue matrices (RTM). These RTMs have been shown to populate with a patient's own cells as part of a healing response. Infiltration by cells such as fibroblasts enables the patient's innate repair mechanisms to guide the regeneration of viable tissue at the surgical repair site. However, these RTMs suffer from a lack of initial mechanical strength and therefore may not be indicated where high initial tensile properties are required, as in abdominal wall repairs. Similarly, RTMs often suffer from an accommodation response post-implant, wherein the implanted material irreversibly and detrimentally deforms in response to the inherent stresses imposed on it. If not managed or corrected, this condition may result in substantial laxity to the repair site, or failure of the graft, which must be corrected in follow up procedures.

There remains a need for controlling the strength and pliability of such implants. It is believed that such control promotes proper healing and revitalization of the tissue or anatomical area being repaired, and also may prevent failure of the implant under biologic load stress within the body.

SUMMARY OF THE DISCLOSURE

The disclosure features implants for tissue repair or tissue reconstruction. The implants comprise a substrate comprising a biotextile, medical textile, or both a biotextile and medical textile, and one or more compliance control stitch patterns sewn or embroidered into the substrate. The substrate may comprise an extracellular matrix. The substrate may be a scaffold such as a hernia repair scaffold, a patch, or a mesh. The substrate may comprise a plurality of layers. The substrate may comprise a biocompatible film.

In some preferred aspects, the substrate comprises a biotextile, and the biotextile comprises an extracellular matrix. The compliance control stitch pattern sewn or embroidered into the substrate comprises a biocompatible polymer. The polymer may comprise polypropylene or polyethylene, and the polypropylene or polyethylene threads or yarn out of which the compliance control stitch pattern is sewn or embroidered may be a monofilament thread or yarn.

In some preferred aspects, the substrate comprises a medical textile comprising a biocompatible polymer. The medical textile may comprise a mesh, and the mesh may comprise a corner-lock stitch pattern. The biocompatible polymer may comprise polypropylene or polyethylene, and the polypropylene or polyethylene threads or yarn out of which the medical textile is made may be a monofilament thread or yarn. The compliance control stitch pattern sewn or embroidered into the substrate comprises a biocompatible polymer. The polymer may comprise polypropylene or polyethylene, and the polypropylene or polyethylene threads or yarn out of which the compliance control stitch pattern is sewn or embroidered may be a monofilament thread or yarn.

The one or more compliance control stitch patterns may comprise a plurality of straight lines oriented along one or more axes of the substrate. The one or more compliance control stitch patterns may comprise a plurality of lines comprising a plurality of repeating angles, which lines are oriented along one or more axes of the substrate. Whether straight lines or lines comprising angles, the compliance control stitch pattern may be uniaxial, biaxial, triaxial, quadaxial, or pentaxial.

In some aspects, the substrate comprises a plurality of compliance control stitch patterns. In aspects where more than one compliance control stitch patterns are present, the compliance control stitch patterns are overlaid. In some aspects, one or more compliance control stitch patterns may be positioned at one or more end regions of the substrate material, and one or more compliance control stitch patterns may be positioned substantially in a central region of the substrate material. Each compliance control stitch pattern (whether at an end region or central region) may be the same or different from other compliance control stitch patterns among the substrate in terms of type, direction, orientation, strength, stretch control, overlaying, thread type, thread thickness, stitch density, and other properties. For example, in some aspects, a first compliance control stitch pattern is sewn or embroidered into the substrate in a first direction or orientation, and a second compliance control stitch pattern is sewn or embroidered into the substrate in a second direction or orientation.

In some aspects, the biotextile or medical textile substrate comprises a plurality of layers, and at least one of the layers comprises a first compliance control stitch pattern, and at least one of the layers comprises a second compliance control stitch pattern. The second compliance control stitch pattern may be the same as or different than the first compliance control stitch pattern. The second compliance control stitch pattern may be oriented in the same or different direction relative to the first compliance control stitch pattern. Multiple layers are possible, each layer having its own compliance control stitch pattern, which may be the same or different from other compliance control stitch patterns among the layers in terms of type, direction, orientation, strength, stretch control, overlaying, thread type, thread thickness, stitch density, and other properties.

The disclosure also features methods for making implants or substrates comprising one or more compliance control stitch patterns. Such methods generally comprise, for example, stitching or embroidering one or more compliance control stitch patterns described or exemplified herein into any substrate described or exemplified herein, which substrate may comprise an implantable biotextile or medical textile.

The disclosure also features methods for repairing or reconstructing tissue in a subject in need thereof. Such methods generally comprise implanting an implant or substrate comprising one or more compliance control stitch patterns sewn or embroidered therein at a location in the body of the subject in need of tissue repair or tissue reconstruction. The tissue may be any tissue in the body, including soft tissue. The tissue may comprise a hernia, such that the implant or substrate is used to repair the herniation. The subject is preferably a human being.

BRIEF DESCRIPTION OF THE DRAWINGS

The disclosure is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

In FIG. 2A, parallel straight stitch patterns are embroidered into a substrate, with straight stitch patterns offering a higher degree of compliance resistance. In FIG. 2B, parallel angled stitch patterns are embroidered into a substrate, with a 20 degree angle between inflection points. In FIG. 2C, parallel angled stitch patterns are embroidered into a substrate, with a 30 degree angle between inflection points. In FIG. 2D, parallel angled stitch patterns are embroidered into a substrate, with a 40 degree angle between inflection points. In FIG. 2E, parallel angled stitch patterns are embroidered into a substrate, with a 50 degree angle between inflection points.

DETAILED DESCRIPTION

Figure 1A:
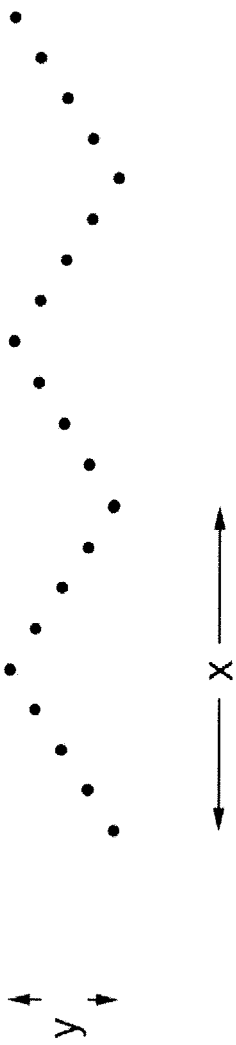
FIG. 1A and FIG. 1B show examples of an angled stitch pattern, in which the angle is wider (FIG. 1A) or narrower (FIG. 1B). A wider angle may result in a wider distance (X) between inflection points in the stitch pattern, and a narrower angle may result in a narrower distance (X) between inflection points in the stitch pattern.
Figure 1B:
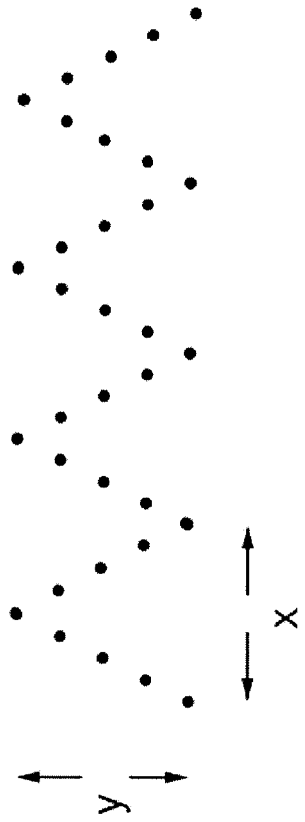

Various terms relating to aspects of the disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

As used herein, "compliance control" means effectuating one or more of control, modulation, influence, or regulation of one or more of the strength, stretching, deformation, displacement, elasticity, flexibility, and resilience of an object, for example, a substrate or an implant, under applied force(s).

It has been observed in accordance with the disclosure that the compliance of a substrate such as a biotextile or medical textile (e.g., a hernia repair scaffold) can be controlled by sewing particular compliance-control stitch patterns into the substrate. With compliance control stitch patterns in place, substrates may be designed to have the capability to stretch or deform in response to certain load forces, such that compliance may be directionally controlled. In addition, it has been observed that the compliance of the substrate may be controlled over time, in order to compensate for natural healing by the body into which the substrate was implanted as well as to compensate for the possibility of continued soft tissue degeneration in the body or to compensate for undesired loss of strength and/or the gain of elasticity of the substrate over time. Accordingly, the disclosure features biotextile and medical textile substrates comprising compliance-control stitch patterns, methods for producing such substrates, and methods for using such substrates, for example, as a medical implant. Compliance is a function of, among other things, strength, stress, elongation, rebound, deformability, and elasticity properties of the particular materials or combination of materials.

Biotextile or medical textile scaffolds are typically used for soft tissue repair or reconstruction and, in this capacity, are generally surgically implanted within the body. Such scaffolds may serve, for example, to replace or reinforce diseased or damaged soft tissue, or to hold internal organs in place in the case of a hernia repair. In some cases, these scaffolds are intended to be a permanent fixture within the body, for example, medical textile scaffolds comprising polymeric threads. In other cases, these scaffolds are intended to be a temporary fixture within the body such that they are made of a material that is gradually resorbed by the body as it is replaced by the body's own tissue, for example, biotextile scaffolds comprising an extracellular matrix. Regardless, patients do not all heal at the same rate, owing to the particular condition in need of repair, and the physical characteristics and conditions of the patient. Accordingly, it is desirable to control the inherent base properties of such scaffolds to accommodate the conditions of individual patients. In addition, it is desirable to compensate for premature breakdown or resorption of the scaffold.

Whether biologic/natural (e.g., biotextiles) or synthetic (e.g., medical textiles), implantable scaffolds have certain inherent strength and stretch properties, based on the particular material from which the scaffold is made as well as how the scaffold was made—e.g., whether assembled with layers, has any added support structures, etc. Over time, particularly after being subject to biomechanical load forces and after being exposed to a patient's immune system, and other natural factors that cannot be controlled, the scaffolds may degrade, weaken, become too elastic, or otherwise lose their original strength and stretch properties, such that the patient is put at risk. Accordingly, the negative conditions from scaffold wear and tear may be mitigated with specially designed stitching or embroidery patterns placed about the scaffold. Such specially designed patterns include compliance control stitching patterns as described and exemplified herein.

Compliance control stitch patterns are sewn, and preferably embroidered, into a substrate. Compliance control stitch patterns preferably are not knitted or weaved into a substrate. Sewing may be by machine or by hand, or by a combination thereof. Sewing may be with a ballpoint needle.

The substrate may be any material into which filaments, yarns, or threads may be sewn according to this disclosure. The substrate may comprise a mesh. A substrate material may comprise a natural or synthetic material, may be a textile, and may be woven or non-woven. The substrate or substrate material may have any thickness, or length and width dimensions. Non-limiting examples of substrate materials include cloth or fabric, lace, leather, silk, linen, nylon, polyester, polypropylene, polyethylene, cotton, satin, wool, bamboo, cashmere, jute, burlap, fleece, felt, spandex, rayon, denim, and other suitable materials, or any combination thereof. In some preferred aspects, the substrate comprises a biotextile or a medical textile. Biotextile or medical textile substrates may be implantable in or on the human body. Thus, a substrate or substrate material may be an implant or a part of an implant.

Biotextiles include biocompatible materials, which may be obtained or derived from living tissue. Biotextiles preferably comprise an extracellular matrix. Living tissue includes, for example dermis/skin tissue (and sub-tissue, extracellular matrices), pericardium, peritoneum, intestine, stomach, forestomach, and other suitable tissues. The animal source may be any suitable animal, including a mammal such as human, pig, cow, or sheep, or may be synthesized, for example, by recombinant expression. Biotextiles may be biodegradable or resorbable. Some non-limiting examples of biotextiles include extracellular matrix-derived tissue scaffolds or patches, autograft tissue, allograft tissue, and xenograft tissue, as well as artificial skin, artificial heart valves, and other implantable prosthetics.

Medical textiles include biocompatible materials, which may include synthetic materials. Some non-limiting examples of medical textiles include hernia repair patches, hernia repair meshes, and hernia repair materials, which may comprise polypropylene, polyethylene, as well as combinations of polypropylene and polyethylene, and other implantable polymers. Substrates comprising polypropylene are preferred in some aspects. Substrates comprising polyethylene, including polyethylene monofilaments are preferred in some aspects.

The substrate may comprise a film, preferably a biocompatible film. The film may comprise a layer placed on the outer surfaces of the substrate, or the film may constitute the entire substrate. Compliance control stitch patterns may be sewn or embroidered into the film, and also may be used to affix the film to the outer surfaces of a substrate.

In some preferred aspects, a substrate comprises a biotextile comprising an extracellular matrix, and the substrate comprises one or more compliance control stitch patterns sewn or embroidered into the substrate. The substrate preferably is for hernia repair, and thus for implantation within the body of a subject. Following implantation, the biotextile may be resorbed by the body over time, and replaced by the body's own extracellular matrices and/or the body's cells. Although the biotextile aspect of the substrate is resorbed or remodeled within the body, the compliance control stitch pattern remains, preferably substantially permanently. Thus, the compliance control stitch pattern preferably comprises a biocompatible polymer that is not substantially resorbed or broken down in the body. In some preferred aspects, the biocompatible polymer comprises polypropylene. In some preferred aspects, the biocompatible polymer comprises polyethylene, which may comprise polyethylene monofilament thread or yarn.

In some preferred aspects, a substrate comprises a medical textile comprising biocompatible polymer threads or yarn, and the substrate comprises one or more compliance control stitch patterns sewn or embroidered into the substrate. The substrate preferably is for hernia repair, and thus for implantation within the body of a subject. The substrate may comprise a mesh, and the mesh may comprise a corner-lock stitch pattern. Following implantation, the medical textile is preferably not substantially resorbed or broken down by the body over time, but rather is substantially permanent. In some preferred aspects, the biocompatible polymer threads or yarn of the medical textile comprises polypropylene. In some preferred aspects, the biocompatible polymer threads or yarn of the medical textile comprises polyethylene. In some preferred aspects, the biocompatible polymer threads or yarn of the medical textile comprise monofilament threads or yarn comprising polyethylene. The compliance control stitch pattern sewn or embroidered into the substrate also is preferably not substantially resorbed or broken down by the body over time and is substantially permanent. Thus, the compliance control stitch pattern preferably comprises a biocompatible polymer that is not substantially resorbed or broken down in the body. In some preferred aspects, the biocompatible polymer of the compliance control stitch pattern comprises polypropylene. In some preferred aspects, the biocompatible polymer of the compliance control stitch pattern comprises polyethylene, which may comprise polyethylene monofilament thread or yarn.

The yarn or threads used to stitch materials and create the compliance control stitch patterns, as well as to create the substrate into which the compliance control stitch patterns are sewn, may be made of any suitable material, and may comprise any suitable weight. The yarn or thread may comprise monofilament yarn or thread, or multi-filament yarn or thread. The thread weight may be a function of the purpose to which the corner-locked mesh is used. The thread weight may range from about 20 weight to about 120 weight. The thread may comprise a denier of from about 1 denier to about 2000 denier. The thread may comprise a denier of at least about 20-denier. The thread may comprise a denier of at least about 30-denier. The thread may comprise a denier of at least about 40-denier. The thread may comprise a denier of at least about 50-denier. The thread may comprise a denier of at least about 60-denier. The thread may comprise a denier of at least about 70-denier. The thread may comprise a denier of at least about 80-denier. The thread may comprise a denier of at least about 90-denier. The thread may comprise a denier of at least about 100-denier. The thread may comprise a denier of at least about 120-denier. The thread may comprise a denier of at least about 150-denier. The thread may comprise a denier of at least about 200-denier. The thread may comprise a denier of at least about 250-denier. The thread may comprise a denier of at least about 300-denier. The thread may comprise a denier of at least about 400-denier. The thread may comprise a denier of at least about 500-denier. The thread may comprise a denier of at least about 600-denier. The thread may comprise a denier of at least about 700-denier.

The yarn may comprise plied yarn or twisted yarn (e.g., z twist or s twist), or may comprise a braided yarn. The thread material may comprise a natural fiber, such as cotton, wool, silk, or other natural material, or may comprise a synthetic fiber such as polyester, nylon, polypropylene, polyethylene, rayon, or other synthetic material. The thread may comprise a monofilament. The thread may comprise a continuous filament. The thread may comprise a staple filament. The thread material may comprise a metal. The thread may comprise a wire, for example, a polymeric wire, composite wire, or metal wire. The thread material preferably is biocompatible and, in some aspects, is resorbable.

The thread material or the medical textile material may comprise a polydioxanone, polycarbonate, polyurethane, poly(alpha-ester), polyglycolide, polylactide (e.g., poly(L-lactic acid), poly(D-lactic acid), and poly(D,L-lactic acid), poly (4-hydroxybutyric acid)—which is a homopolymer of 4-hydroxybutyrate (4HB), and belongs to a diverse class of materials called polyhydroxyalkanoates (PHAs)—and poly (lactide-co-glycolide)), polycaprolactone, poly(propylene fumarate), polyanhhydride, polyacetal, polycarbonate (e.g., poly(trimethylene carbonate)), poly(ortho ester), polyphosphazene, polyphosphoester, polytetrafluoroethylene, polyethylene terephthalate, or any combination or co-polymer thereof. Polypropylene, polyester, and polyethylene are preferred, with monofilament polyethylene more preferred. The thread material preferably is biocompatible and, in some aspects, is resorbable. Any biodegradable polymer known in the art may be used. For example co-polymers or mixtures of such polymers may modulate the properties of the threads or medical textile, including to make the threads or medical textile more or less capable of stretching, or more or less stiff, or stronger or weaker, or for long-term, mid-term, or short-term potential for resorption/biodegradation.

The yarn or thread may be colored. Colors may indicate a proper orientation of the mesh or material+mesh, for example, the colors may indicate the proper orientation for implantation of a hernia repair mesh. Colors may indicate a front or back.

Thread or yarn is preferably stitched or embroidered into a substrate to form a compliance control stitch pattern in the substrate. The substrate having the compliance control stitch pattern may then be used in a surgical implantation procedure, for example, for purposes of soft tissue repair or regeneration. The compliance control stitch pattern modulates the strength and/or the capacity of the substrate to stretch, thereby allowing the substrate to stretch or resist stretching, conform to, resist, or otherwise accommodate load, compression, tension, torsion, relaxation, shear, bending, and other forces imposed on the substrate by patient movement once the substrate is implanted within the patient's body.

The compliance control stitch pattern further strengthens the base properties of the substrate material such that the substrate is not stretched to or beyond its failure point by load, compression, tension, torsion, relaxation, shear, bending, and other forces imposed on the substrate by patient movement once the substrate is implanted within the patient's body.

Figure 9A:
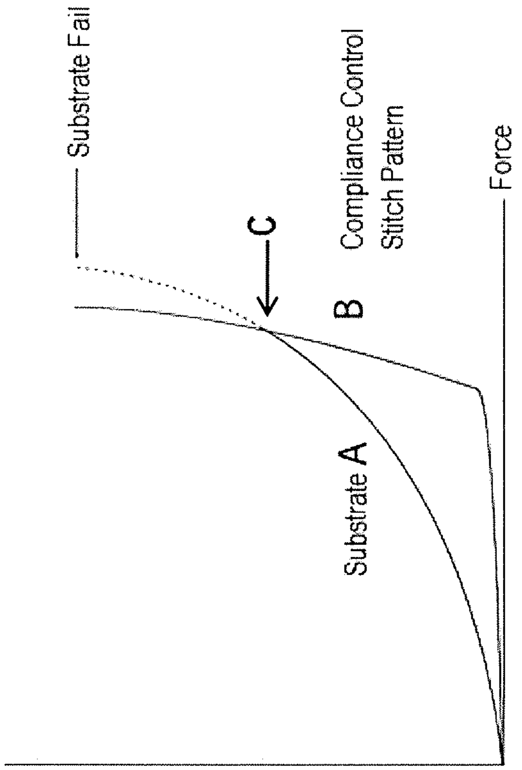
FIG. 9A shows a graphical illustration of compliance control. In this figure, line A represents the properties of a biologic substrate, and as a force (y axis) is applied to the substrate, a resultant extension (x axis) occurs until the substrate fails (tissue break point). Line B represents the contribution of the supporting compliance control stitching patterns: at low applied forces, the stitch pattern offers minimal compliance control, as the compliance is dictated by the properties of the biologic substrate, but as the force is increased, the stitch pattern elongates, and then exerts increasing compliance control until the point (point C) where load bearing is transferred from the substrate to the stitch pattern. The dotted line indicates a safety factor, showing that the compliance control exerted by the stitch pattern prevents the substrate from reaching its failure point from the force applied.

It is believed that compliance control stitch patterns may be configured to provide that stretching and deformability of the implanted substrate will be less than the ultimate failure point of the substrate material, which, in turn, provides a safety factor that ensures that the substrate will not fail due to excessive loading. For example, the compliance control stitch patterns allow the substrate to stretch and move within the body as needed, but not tear apart under stress. Sec, e.g., FIG. 9A.

The strength and integrity of the implanted substrate is thus maintained by toggling the force response back and forth between the substrate and the compliance control stitch pattern as needed and in response to stress forces within the body. At lower stress forces, the substrate may stretch within a defined limit, but at higher stress forces, including extreme forces that may push the limits of the substrate material, the compliance control stitch pattern bears at least some of the load and, thus, prevents a failure of the implant. The force-shifting stress response may accommodate additional changes in the patient's characteristics, for example, weight gain or loss, aging, disease or degeneration advancement, and other physical characteristics of the patient that may affect how the substrate material responds to movement and other forces within the body. For example, force-shifting may accommodate short-term forces such as those caused by coughing, sneezing, jumping, or reflexive movements.

Compliance control of the substrate may be accomplished by one or a combination of a particular stitch pattern on the whole, the type of thread or yarn used to stitch the compliance control pattern, the type of stitching used (e.g., chain stitch, Merrow stitch, lock stitch, zigzag stitch, straight stitch, running stitch, back stitch, satin stitch, or combinations thereof), angles of the stitch pattern, density of stitches, stitch direction, and the overlay of one or more stitch patterns. Additional components and properties that may be varied to achieve a desired level of compliance control include the substrate material, stacking of substrate material layers, the size of the substrate, the diameter and/or denier of the thread/yarn used to impart the compliance control stitch pattern, location and/or orientation of the implanted substrate within the body, and other factors that are known to the medical practitioner or patient.

Figure 1C:
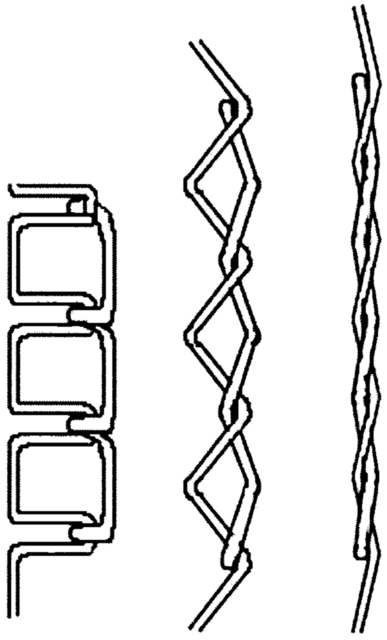
FIG. 1C shows an example of compliance control from stitches. Compliance modulation may relate, in part, to the thickness of the thread material. For example, if the thread material is thick, changing the shape of the stitch, or modulating the length of stitch between thread interlace points may modulate the compliance exerted by the stitch pattern.

The substrate may comprise any suitable thickness, size, or dimensions. These properties may relate, in part, to the intended location of the substrate once implanted in the body, as well as particular patient needs, condition, or characteristics. The thread or yarn may comprise any suitable strength or thickness, and the thread or yarn may be sewn or embroidered into the substrate material at any particular stitch density/number of stitches, as appropriate for the desired reinforcement and compliance control imparted into the substrate (e.g., FIG. 1C).

Figure 5:
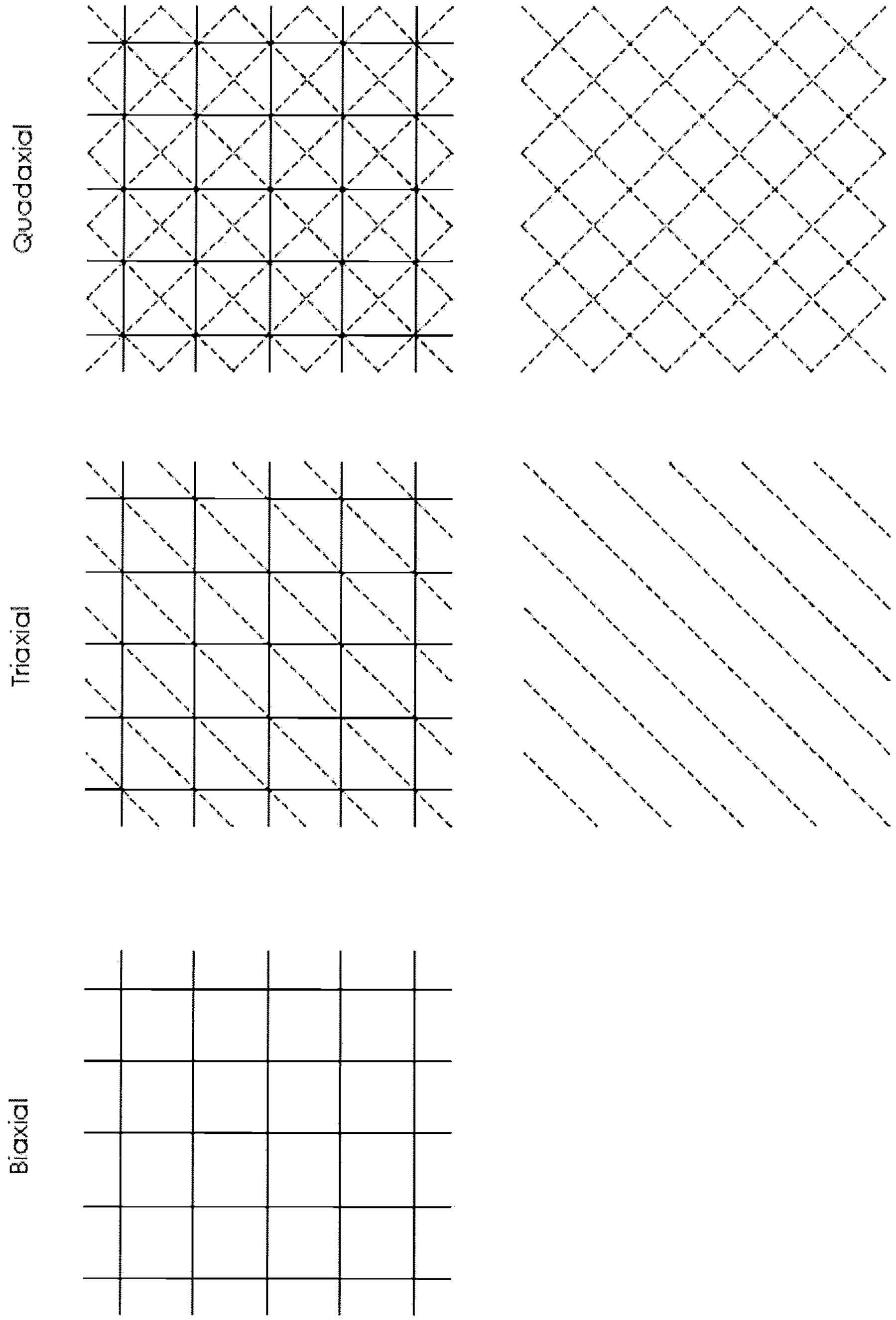
FIG. 5 shows examples of a biaxial compliance control stitch pattern (upper left panel), a triaxial compliance control stitch pattern (upper center panel), and a quadaxial compliance control stitch pattern (upper right panel). In this example of a triaxial compliance control stitch pattern, a stitch pattern is sewn at a diagonal across a biaxial grid pattern. The lower center panel shows the diagonal stitch pattern (dotted lines). In this example of a quadaxial compliance control stitch pattern, two diagonal stitch patterns in opposing directions are sewn across a biaxial grid pattern. The lower right panel shows the opposing diagonal stitch patterns (dotted lines).
Figure 8A:
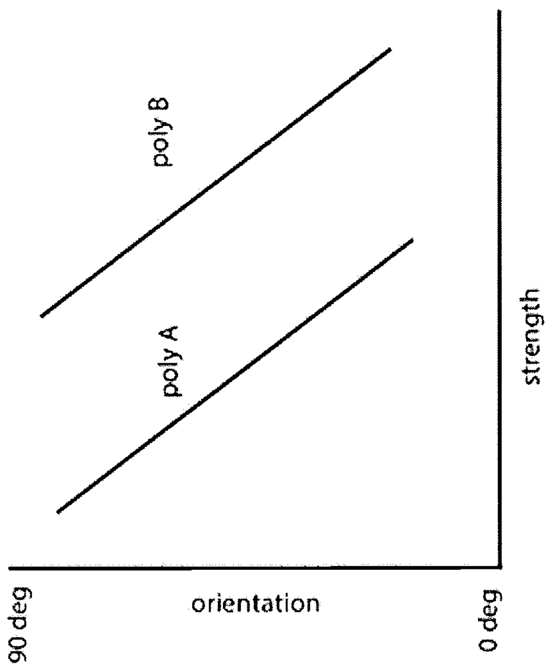
FIG. 8A illustrates strength characteristics of a substrate sewn with different polymer types (poly A versus poly B). The graph illustrates the orientation of the stitch pattern direction on the y-axis and resulting effects on overall strength of the device on the x-axis. Orientation in this graph refers to the direction of a hypothetical stitch pattern in relation to load applied to the substrate. A stitch pattern is at 0 degrees when it is in-line with the direction of load. A stitch pattern orientation of 90 degrees would lie at an orientation directly perpendicular to a proposed uni-axial loading. As stitch pattern lines approach 0 degrees, resultant strength of the embroidered substrate is controlled and directed via the substrate properties and stitch patterns.
Figure 8B:
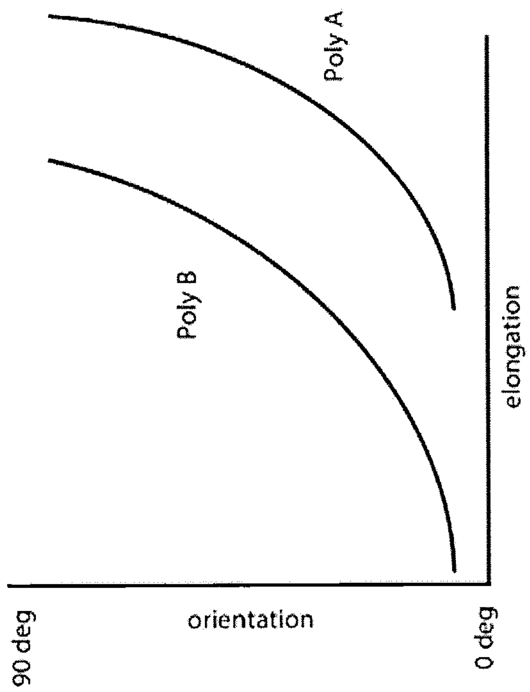
FIG. 8B illustrates elongation characteristics of a substrate sewn with different polymer types (poly A versus poly B). Elongation may be controlled for any load which occurs at any point within the bracketing plots resulting from substituting polymer A with polymer B.

Compliance control may be uniaxial, such that control is exerted in, for example, along a single axis such as a horizontal axis or a vertical axis or a horizontal axis. Compliance control may be biaxial, such that control is exerted along two different axes, such as both a horizontal and vertical axis, or both a horizontal and diagonal axis, or both a vertical and diagonal axis, or two different diagonal axes. Compliance control may be triaxial, such that control is exerted along three different axes, such as a horizontal, vertical, and diagonal axis, or three different diagonal axes. Compliance control may be quadaxial, such that control is exerted along four different axes, such as a horizontal, vertical, and two different diagonal axes, or along four different diagonal axes. Compliance control may be exerted along five of more different axes in some aspects. and may involve individual layers, a subset of multiple layers, or the entire hybrid device. Thus, compliance control may be in a single directional orientation, or may be in multi-directional orientations across or through the device (e.g., FIG. 8A and FIG. 8B); or may be isotropic, about the substrate. A representation of a biaxial, triaxial, and quadaxial compliance control stitch pattern is shown in FIG. 5.

Figures 2A, 2B, 2C, 2D, 2E:
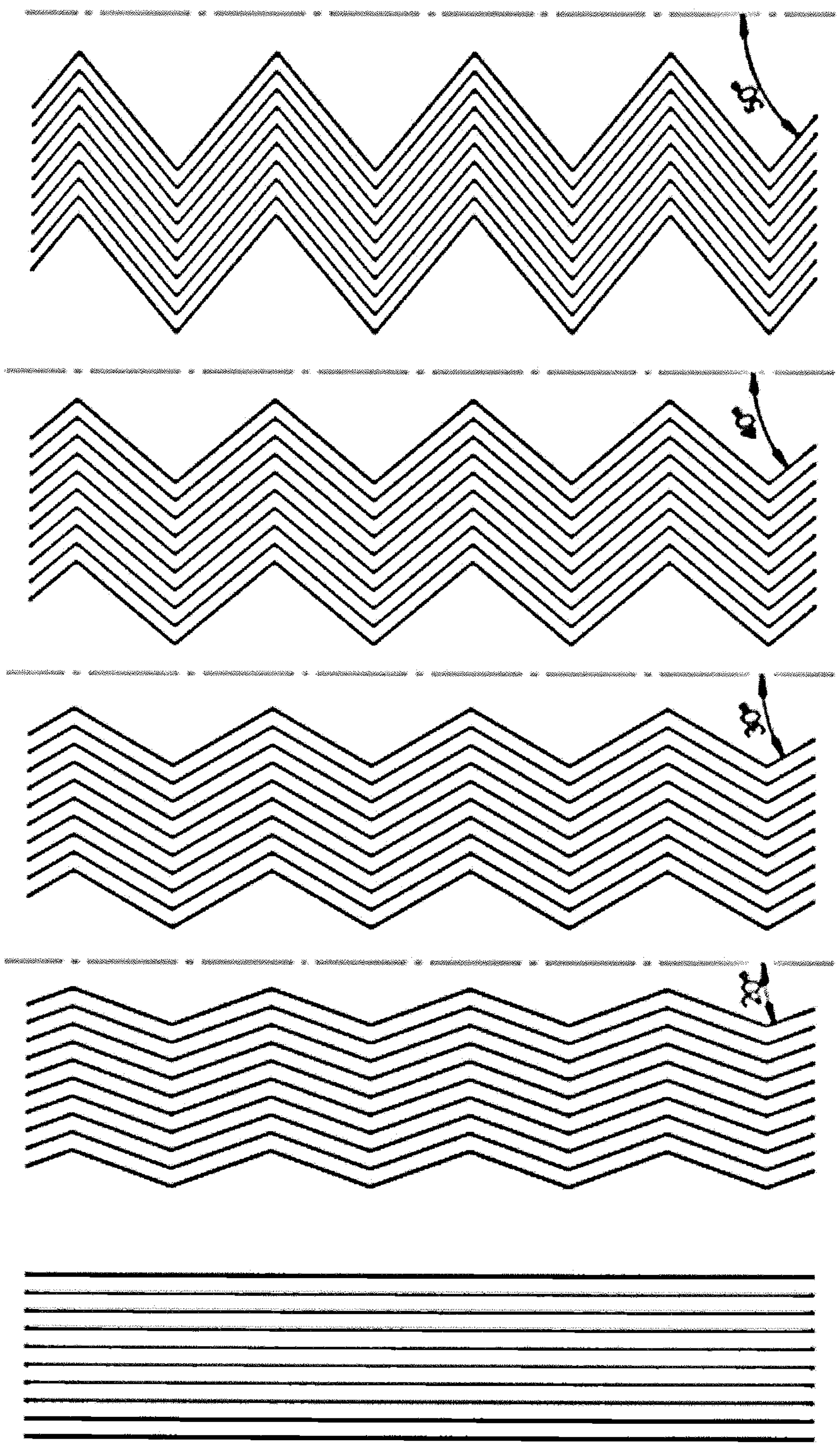
FIGS. 2A through 2E show different compliance-control stitch patterns.
Figure 11A:
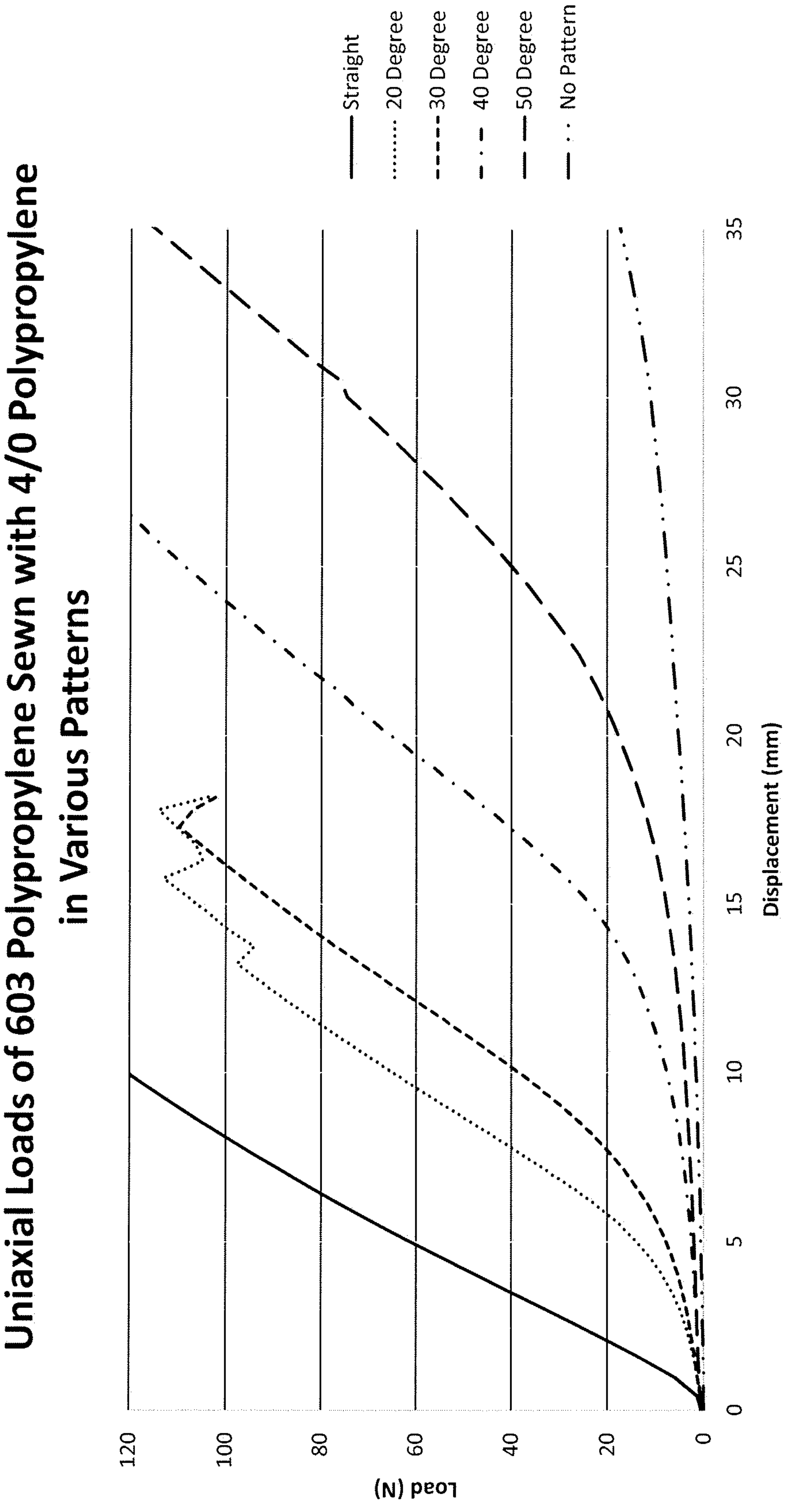
FIG. 11A shows the results of a comparative compliance control strain study (strain load at 16 N/cm) for a synthetic polymer mesh substrate material having five different types of compliance control stitching patterns (4/0 polypropylene threads). The compliance control stitching patterns were either a straight stitch pattern or a 20 degree, 30 degree, 40 degree, or 50 degree angled stitch pattern (e.g., FIGS. 2A-2E). The substrate without any compliance control stitching was tested in parallel for comparison. Each substrate was subject to a strain load, and the displacement of the substrate under the load was measured (in mm). Straight stitch compliance control patterns strongly resisted displacement/stretching of the substrate, whereas angled compliance control stitch patterns allowed for increased displacement, which displacement was greater as the angle increased.
Figure 11B:
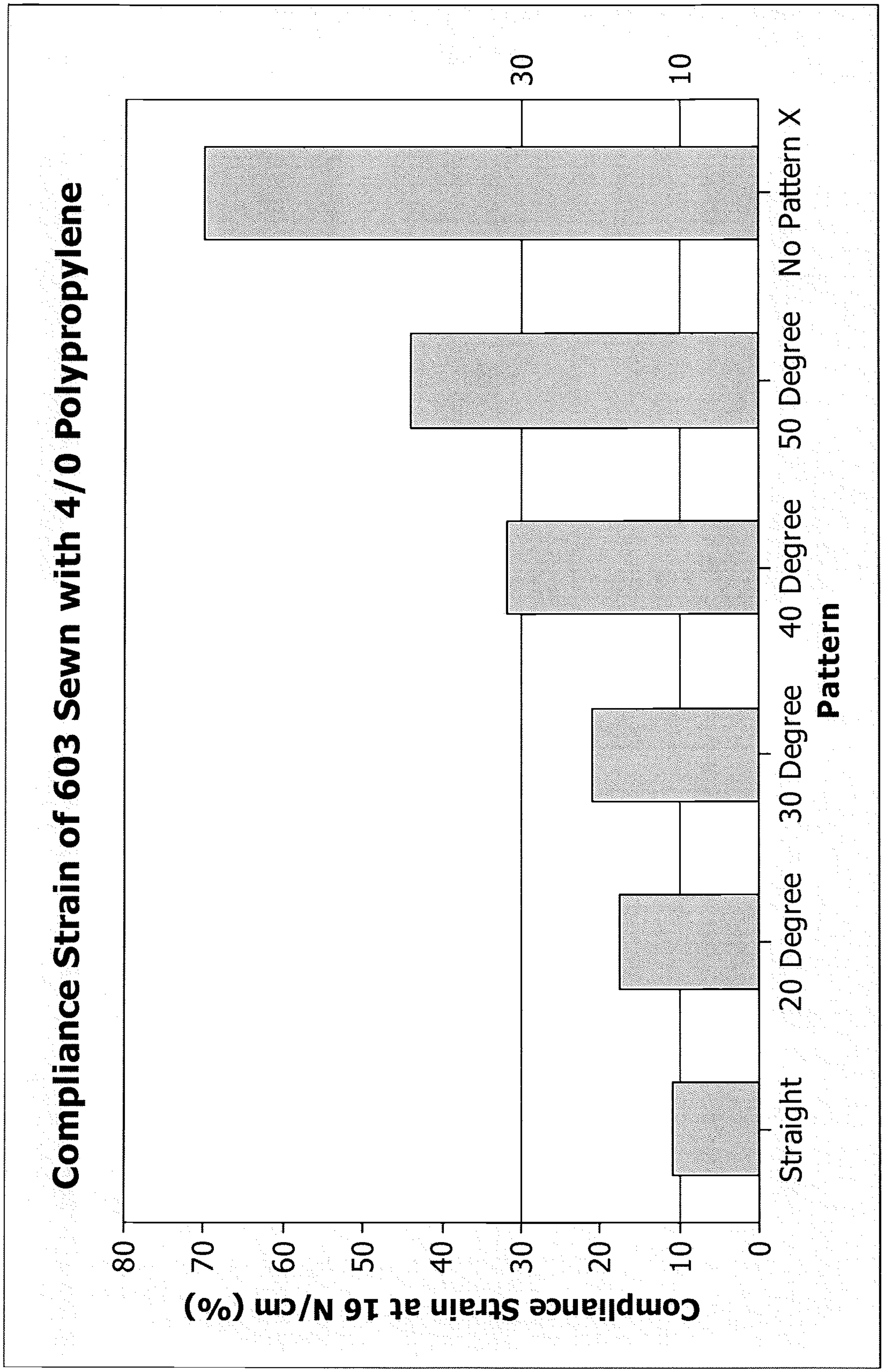
FIG. 11B shows the results of the compliance control study from FIG. 11A in a bar graph format. Compliance strain is represented as a percentage.

Compliance control stitch patterns may comprise one or more straight lines (FIG. 2A). Where a plurality of straight lines are employed, they may be sewn/embroidered in parallel, or in a grid pattern (e.g., FIG. 5 and FIG. 7B). It is believed that straight stitch patterns exhibit the highest degree of compliance control, particularly in the direction of the straight stitch axis. FIG. 11A and FIG. 11B demonstrate minimal displacement upon the stretching of substrates having a compliance control stitch pattern comprising a plurality of straight lines. Thus, a straight or linear stitch pattern may serve to limit deformation (stretching) is in line with the axis of the stitch line.

Compliance control stitch patterns may comprise a plurality of angles, which may comprise a plurality of repeating angles (FIG. 1A, FIG. 1B, and FIGS. 2B-2E). Where a plurality of angled lines are employed, they may be sewn/embroidered in parallel (e.g., FIGS. 2B-2E), or in a grid pattern (not shown). The angle is formed between inflection points in the stitch pattern (FIG. 1A and FIG. 1B), and each angle may be from about 0 degrees to about 180 degrees, or at any integer between 0 degrees and 180 degrees, inclusive (e.g., 1 degrees, 2 degrees, 3 degrees, 4 degrees, 5 degrees, 6 degrees, 7 degrees, etc.). It is preferred that the same angle is used throughout a given stitch line, but in some aspects, a combination of different angles may be used throughout a given stitch line. Thus, by way of example and for illustration purposes only a stitch pattern may comprise a plurality of repeating 30 degree angles, or may comprise a plurality of alternating 30 and 50 degree angles, or may comprise any combination of angles. Thus, an angled stitch pattern may serve to limit deformation (stretching) is in line with the axis of the stitch line.

It is believed that angles having lower degrees exert a higher level of compliance control upon the substrate, and that angles having higher degrees exert a lower level of compliance control upon the substrate. Thus, for example, a stitching pattern comprising a plurality of 20 degree angled stitch patterns will exert a higher level of compliance control upon a substrate than a stitching pattern comprising a plurality of 50 degree angled stitch patterns. Sec, e.g., FIG. 11A and FIG. 11B. It is believed that angled stitch patterns exert a lower level of compliance control upon the substrate relative to straight stitch patterns, because the angles must flatten out (under tension) before imparting stretch resistance.

Density of the stitch pattern is believed to be important to compliance control. For example, more reinforcing stitches at least will impart strength or reinforcement into the substrate. But stitching density may also be relevant to stretch resistance. For example, a higher density of compliance control stitches will make the substrate more resistant to stretching relative to a lower density of compliance control stitches. Density may comprise the number of stitches within a stitch pattern. Density may comprise the number of adjacent or parallel stitch patterns and/or the proximity of adjacent or parallel stitch patterns to each other or other stitch patterns (e.g., FIG. 2A-2E).

In the case of parallel straight stitches or angled stitch patterns, placing such stitch patterns closer together allows for more stitch patterns to be sewn or embroidered into the substrate. High density parallel stitch patterns may comprise adjacent stitch patterns placed from about 0.5 mm to about 5 mm apart, may comprise adjacent stitch patterns placed from about 1 mm to about 4 mm apart, from about 1 mm to about 3.5 mm apart, from about 1 mm to about 3.3 mm apart, from about 1 mm to about 3.2 mm apart, from about 1 mm to about 3.1 mm apart, from about 1 mm to about 3 mm apart, from about 1 mm to about 2.8 mm apart, from about 1 mm to about 2.6 mm apart, from about 1 mm to about 2.5 mm apart, from about 1 mm to about 2.3 mm apart, from about 1 mm to about 2 mm apart, from about 2 mm to about 3.5 mm apart, from about 2 mm to about 3.3 mm apart, from about 2 mm to about 3.1 mm apart, from about 2 mm to about 3 mm apart, from about 2 mm to about 2.8 mm apart, from about 2 mm to about 2.5 mm apart, or from about 2 mm to about 2.2 mm apart.

Stitches may be from about 0.5 mm to about 12 mm per stitch. See, e.g., FIG. 1C. Stitches may be from about 1 mm to about 7 mm per stitch, from about 1 mm to about 6 mm per stitch, from about 1 mm to about 5 mm per stitch, from about 2 mm to about 6 mm per stitch, from about 2 mm to about 5 mm per stitch, from about 2 mm to about 4 mm per stitch, from about 3 mm to about 6 mm per stitch, or from about 3 mm to about 5 mm per stich.

Figure 3:
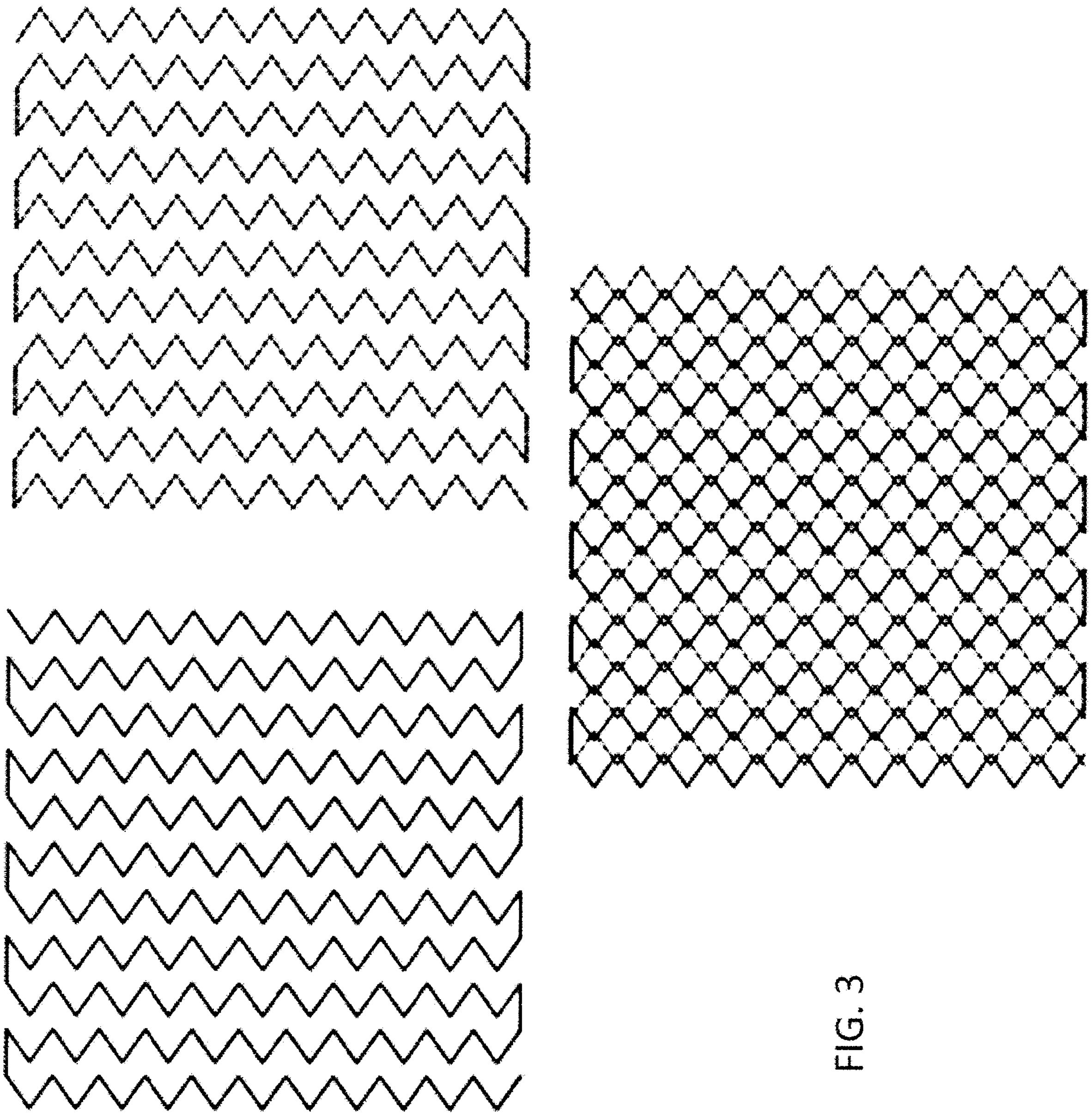
FIG. 3 shows an example of a corner-lock stitch pattern (lower panel) that is formed by stitching two patterns into the substrate (upper left panel (solid line) and upper right panel (dotted line)). The upper and lower threads of the second pattern (dotted line) envelope the upper and lower threads of the first pattern (sold line) adjacent to the vertex of the angled pattern. The overlapping threads interlock at the angle vertices, such that the resulting stitch pattern resists stretching. The corner-lock stitch pattern may be sewn or embroidered based on angled stitch patterns, such as those shown in FIGS. 2A-2E. It is believed that a corner-lock stitch pattern yields a more stable mesh-like configuration, for example, in cases where the substrate material resorbs or prematurely breaks downs. Corner-lock stitch patterns resist stretching along certain axes and permit stretching along other axes.

In some aspects, corner-locked stitch patterns may be used to exert compliance control. Thus, a compliance control stitch pattern may comprise a corner-lock stitch pattern. Such corner-locked stitch patterns are described, for example, in U.S. application Ser. No. 15/196,439, incorporated by reference herein. See also, FIG. 3.

In some aspects, a corner-lock stitch pattern comprises a first pattern of a first upper thread and a first lower thread comprising one or more curves, one or more angles, or a combination of one or more curves and one or more angles, and a second pattern of a second upper thread and a second lower thread comprising one or more curves, one or more angles, or a combination of one or more curves and one or more angles. Yarn may be used in place of thread in the first pattern, second pattern, or both. At least one of the one or more curves or the one or more angles of the second pattern overlap at least one of the one or more curves or the one or more angles of the first pattern. One or more of the overlaps comprises a corner-lock stitch pattern comprising one or more thread interlace points and two or more thread overlays in which the second upper thread and second lower thread envelope the first upper thread and first lower thread. In preferred aspects, one or more of the overlaps comprises a corner-lock stitch pattern comprising two thread interlace points and two thread overlays in which the second upper thread and second lower thread envelope the first upper thread and first lower thread.

In some aspects, the first pattern and the second pattern each comprise one or more angles, and one or more of the overlaps comprises a corner-lock stitch pattern comprising one or more thread interlace points proximal to the vertex of each angle. In some aspects, the first pattern and the second pattern each comprise one or more angles, and one or more of the overlaps comprises a corner-lock stitch pattern comprising one or more thread interlace points in close proximity to the vertex of each angle. In some aspects, the first pattern and the second pattern each comprise one or more angles, and one or more of the overlaps comprises a corner-lock stitch pattern comprising one or more thread interlace points substantially at the vertex of each angle. In any such case, the two or more thread overlays may be proximal to the vertex, or may be in close proximity to the vertex, or may be substantially at the vertex.

The first pattern may comprises a plurality of angles forming one or more polygonal rings. The second pattern may comprise a plurality of angles forming one or more polygonal rings. At least one ring of the second pattern may overlap at least one ring of the first pattern, and each overlapping ring preferably comprises a corner-lock stitch pattern. The corner-lock stitch pattern may comprise one or more thread interlace points, which thread interlace points may be proximal to the vertex of overlapped angles from each overlapped ring, or may be in close proximity to the vertex of overlapped angles from each overlapped ring, or may be substantially at the vertex of overlapped angles from each overlapped ring. In any such case, the two or more thread overlays may be proximal to the vertex, or may be in close proximity to the vertex, or may be substantially at the vertex. The one or more polygonal rings may comprise substantially an irregular shape, or a diamond, square, rhomboid, rectangular, or parallelogram shape, or any combination thereof.

In some aspects, the first pattern and the second pattern each comprise one or more curves, and one or more of the overlaps comprises a corner-lock stitch pattern comprising one or more thread interlace points proximal to the vertex of each curve. In some aspects, the first pattern and the second pattern each comprise one or more curves, and one or more of the overlaps comprises a corner-lock stitch pattern comprising one or more thread interlace points in close proximity to the vertex of each curve. In some aspects, the first pattern and the second pattern each comprise one or more curves, and one or more of the overlaps comprises a corner-lock stitch pattern comprising one or more thread interlace points substantially at the vertex of each curve. In any such case, the two or more thread overlays may be proximal to the vertex, or may be in close proximity to the vertex, or may be substantially at the vertex.

The first pattern may comprise a plurality of curves forming one or more circular rings. The second pattern may comprise a plurality of curves forming one or more circular rings. At least one ring of the second pattern may overlap at least one ring of the first pattern, and each overlapping ring preferably comprises a corner-lock stitch pattern. The corner-lock stitch pattern may comprise a thread interlace point, which thread interlace point may be proximal to the vertex of the overlapped curve of each ring, or may be in close proximity to proximal to the vertex of the overlapped curve of each ring, or may be substantially at the vertex of the overlapped curve of each ring. In any such case, the two or more thread overlays may be proximal to the vertex, or may be in close proximity to the vertex, or may be substantially at the vertex.

Figure 4A:
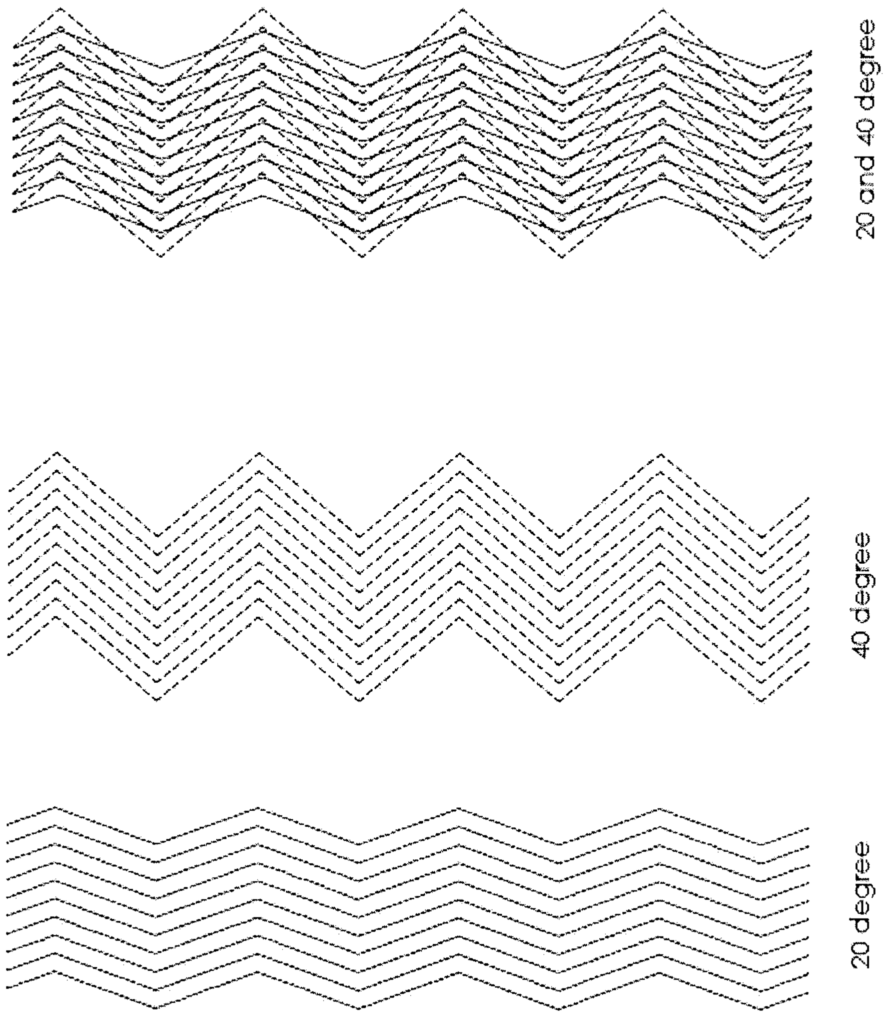
FIG. 4A shows an example of overlaid compliance control stitch patterns. As shown, a stitch pattern comprising repeating 20 degree angles (solid lines) is overlaid by a stitch pattern comprising repeating 40 degree angles (dotted lines).

Compliance control stitch patterns may be overlaid. Thus, for example, a second compliance control stitch pattern may be sewn or embroidered over a first compliance control stitch pattern. By way of example, but not of limitation, FIG. 4A shows an overlay of a first angled (20 degrees) compliance control stitch pattern and a second angled (40 degrees) compliance control stitch pattern. More than two stitch patterns may be overlaid, including two or more compliance control stitch patterns.

Figure 4B:
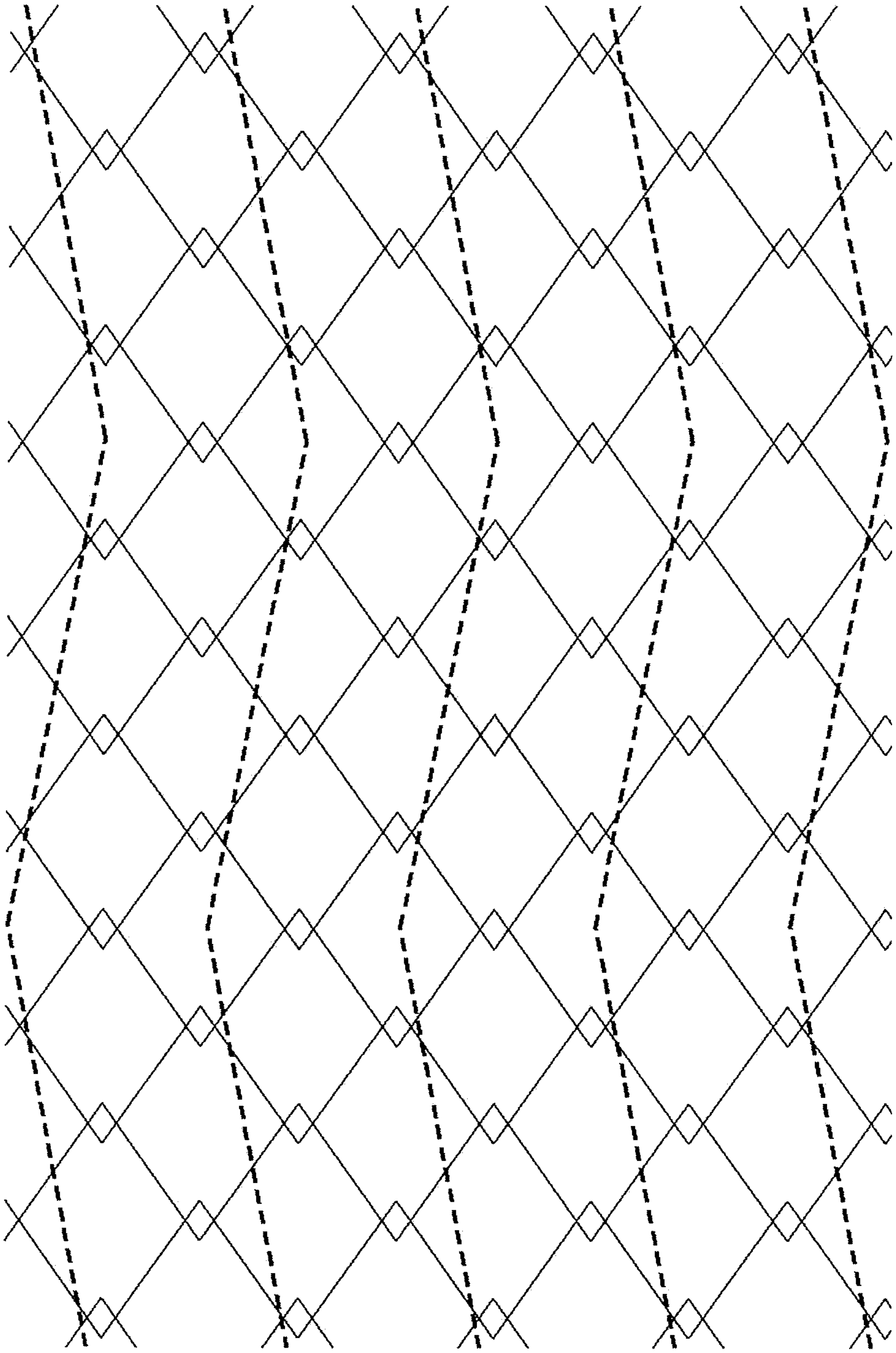
FIG. 4B shows an example of a compliance control stitch pattern (shown as dashed zigzagged lines) overlaid with a corner-lock stitch pattern. In some aspects, a mesh substrate formed from a corner-lock stitch pattern may comprise a compliance control stitch pattern sewn into the mesh.

One or more compliance control stitch patterns may be overlaid with a corner-lock stitch pattern, as shown in FIG. 4B. For example, in some aspects, a substrate comprises a mesh, and the mesh comprises a corner-lock stitch pattern. The one or more compliance control stitch patterns may be sewn into the corner-lock stitch pattern mesh in order to impart compliance control into the corner-lock mesh. A substrate, including a mesh, comprising a corner-lock stitch pattern may be any substrate described in U.S. application Ser. No. 15/196,439

Compliance control stitch patterns may be sewn or embroidered at a different direction relative to another compliance control stitch pattern. Thus for example, a second compliance control stitch pattern may be sewn into the substrate material in a direction that is diagonal (or perpendicular) to the direction of another compliance control stitch pattern sewn into the substrate material. By overlaying compliance control stitch patterns, directional control (e.g., in more than one direction) of stretch resistance may be imparted into the substrate material. Overlaying compliance control stitch patterns may bring about the biaxial, triaxial, and quadaxial compliance control as described herein (FIG. 5).

Figure 6A:
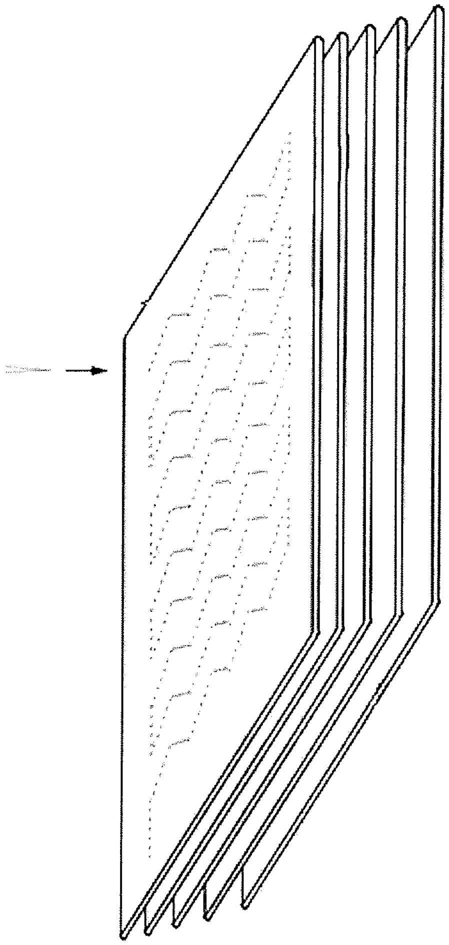
FIG. 6A shows an example a biologic substrate having multiple layers (in an exploded view) with a supporting compliance-control stitch pattern being embroidered into the substrate through the layers.
Figure 6B:
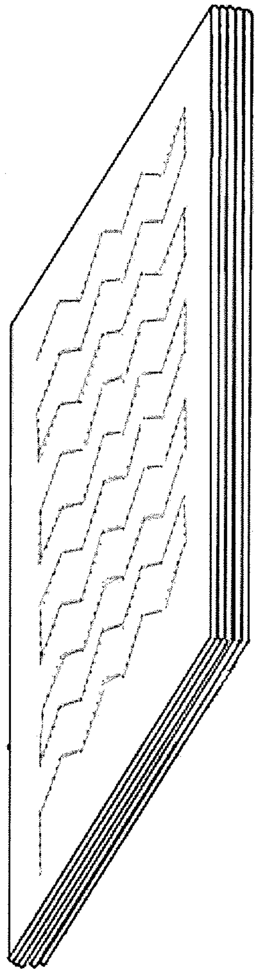
FIG. 6B shows an example of the biologic substrate from FIG. 6A in an assembled view, with the compliance control stitch pattern having been embroidered into the substrate though the layers. The compliance control stitch pattern may aid in securing layers together.
Figure 7A:
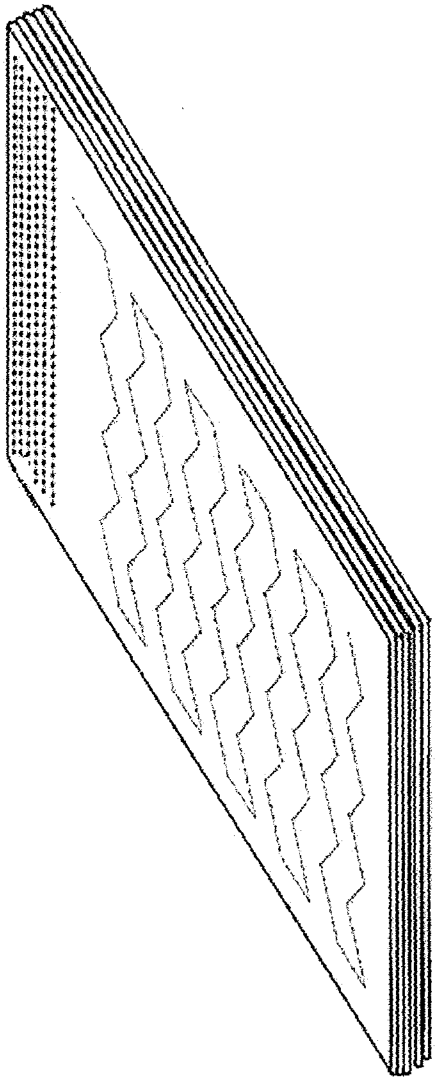
FIG. 7A shows an example of two separate compliance control stitch patterns used in combination. In such an example, a straight stitch pattern, as shown near the top of the substrate, may impart relatively rigid stretch resistance in areas of the substrate at and adjacent to the straight stitch pattern. In addition, an angled stitch pattern, as shown near the bottom of the substrate, may impart a relatively compliant stretch resistance in areas of the substrate at and adjacent to the straight stitch pattern.
Figure 7B:
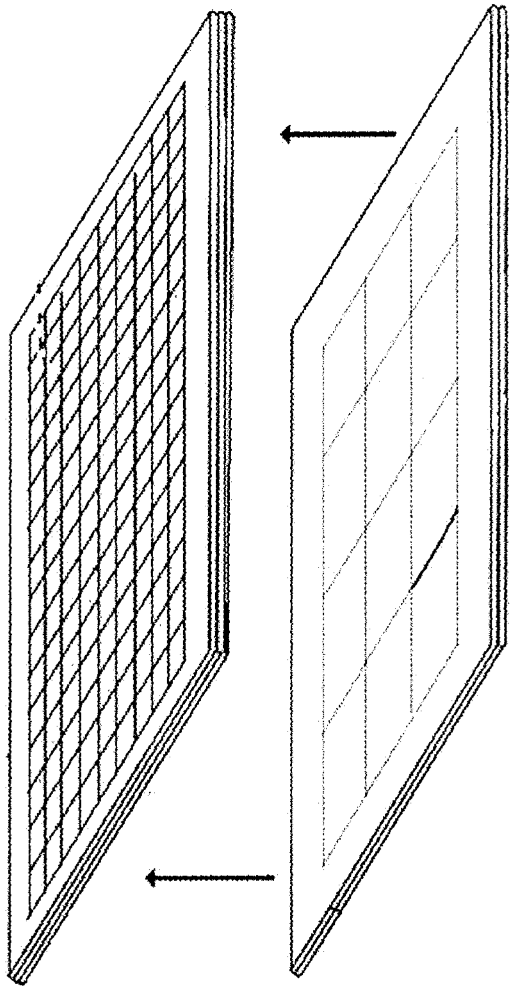
FIG. 7B shows an example of two separate compliance control stitch patterns used in combination, but among different sub-layers of a multiple layered substrate. As shown, the top layers of the substrate, having a higher density of stitch patterns, may be more rigid and stretch-resistant relative to the bottom layers, which have a lower density of stitch patterns.

Layering of substrate materials may contribute to compliance control. As shown, for example, in FIG. 6A and FIG. 6B, substrate materials may be layered together, optionally with an adhesive between layers. Compliance control stitch patterns may be sewn or embroidered into a layered substrate material in any configuration described or exemplified herein. For example, a sewing machine In preferred aspects, compliance control stitch patterns are sewn or embroidered through all layers of a layered substrate (FIG. 3B). In some aspects, combinations of different compliance control stitch patterns may be sewn or embroidered into different portions of the substrate, for example, as shown in FIG. 7A. In some aspects, the compliance control stitch patterns may be varied among layers or subsets of layers, for example, as shown in FIG. 7B. Layers can be sewn together to form a sub-layer set with desired compliance characteristics (e.g., one sub-layer may be more or less compliant than another sub-layer, or multiple sub-layers may be more or less compliant than other sub-layers). In some aspects, one or more sub-layers sets with different compliance characteristics may be sewn together, the stitches that bridge sub-layers together optionally also having independent compliance characteristics (e.g., more or less compliance than the compliance of the sub-layers of the substrate material being sewn together).

When implanted into the body, a substrate may be oriented in a particular direction or configuration, and/or may span different regions of the body such that certain subsections of the substrate may be subject to different mechanical load stresses than other subsections of the substrate, for example, due to the relative positioning of the substrate within the body. Thus, different compliance control stitch patterns may be sewn or embroidered throughout the substrate, including at different locations of the substrate in order to accommodate the expected stresses and forces likely to be encountered by a given portion of the substrate in the body.

For example, if one or more ends of the substrate are to be positioned in the body in an area that is subject to movement but the middle area of the substrate is to be positioned in the body in an area that does not move significantly, then the compliance control stitch pattern may be more stretch-permissive and strong at the ends, but more stretch-restrictive and less strong in the middle. In this configuration, for example, the ends of the substrate may have an angled stitch compliance control stitch pattern and the center area of the substrate may have a straight stitch or small angled stitch compliance control stitch pattern (e.g., FIG. 7A). The converse configuration may also be used, for example, with straight stitch compliance control stitch pattern at the ends in order to resist movement stress, and an angled stitch compliance control stitch pattern in the center area of the substrate. Any configuration and/or combination of compliance control stitch patterns may be used, as appropriate for particular patient needs, condition, or characteristics.

In another example, the front or anterior of the substrate may have a different compliance control stitch pattern than the rear or posterior of the substrate. This configuration may be used, for example, in time delay compliance control applications, or in situations where more or less stretch capacity or more or less strength is needed on the internal side of the implanted substrate material relative to the external side. Attaining different compliance control stitch patterns on the front or anterior versus the rear or posterior of the substrate may be accomplished, for example, by sewing or embroidering one type of compliance control stitch pattern (or combination of different compliance control stitch patterns) into the sub-layers that will constitute the front or anterior of the substrate, and a different type of compliance control stitch pattern (or combination of different compliance control stitch patterns) into the sub-layers that will constitute the rear or posterior of the substrate (e.g., FIG. 6B).

More than two sub-layers (e.g., front/anterior and rear/posterior) are possible, such that the substrate-implant may comprise one or more sub-layers in the center/between the front/anterior and rear/posterior sub-layers. The one or more central sub-layers may also have compliance control stitching patterns (or combination of different compliance control stitch patterns) that differ from the compliance control stitching patterns (or combinations thereof) in the front/anterior and/or the rear/posterior sub-layers.

The direction of stitching may also factor into compliance control of the substrate. Thus, in some aspects, a compliance control stitch pattern may be stitched or embroidered into a substrate in a particular direction or orientation. The direction or orientation of the stitch pattern may relate to, for example, by the orientation or location of the substrate once implanted in the body, as well as particular patient needs, condition, or characteristics. Multiple compliance control stitch patterns may be stitched or embroidered into a substrate, each in a different direction or orientation, or at least one of which in a different direction or orientation relative to a counterpart compliance control stitch pattern in the substrate. Different thread types may be used, in order to impart different strength and/or compliance characteristics into the substrate according to their orientations (e.g., FIG. 8A and FIG. 8B).

Compliance control stitching or compliance control patterns may also be used to modulate the isotropy of a substrate. For example, a substrate may (e.g., in the absence of compliance control stitch patterns) have anisotropic compliance characteristics. By sewing or embroidering a compliance control stitch pattern to such a substrate, the combination (the substrate with compliance control stitch patterns) may be more isotropic relative to the naked substrate. Conversely, the compliance control stitch pattern may allow the combination to be anisotropic or less isotropic in circumstances where the substrate material is isotropic in the absence of the compliance control stitch pattern. Thus, compliance control stitching may alter/modulate the isotropic behavior of the substrate.

Biotextiles and medical textile substrate materials are commonly used as implants in soft tissue repair and regeneration applications, for example, hernia repair, or breast reconstruction. In some cases, the implanted substrate provides a base scaffold that supports the repaired area until the patient's body self-repairs, for example, as the patient's cells infiltrate the substrate material and generate new tissue. In other cases, the patient's body will not completely self-repair, or that the repair will not be sufficiently strong such that the implanted substrate stands in for or permanently reinforces the natural tissue. In the former case, it is often desired that the substrate remain in place until the repaired tissue can shoulder the load forces, though this may be a slow and developing process that takes place over time. In either case, there is a possibility of premature weakening or failure of the substrate material.

Figure 9B:
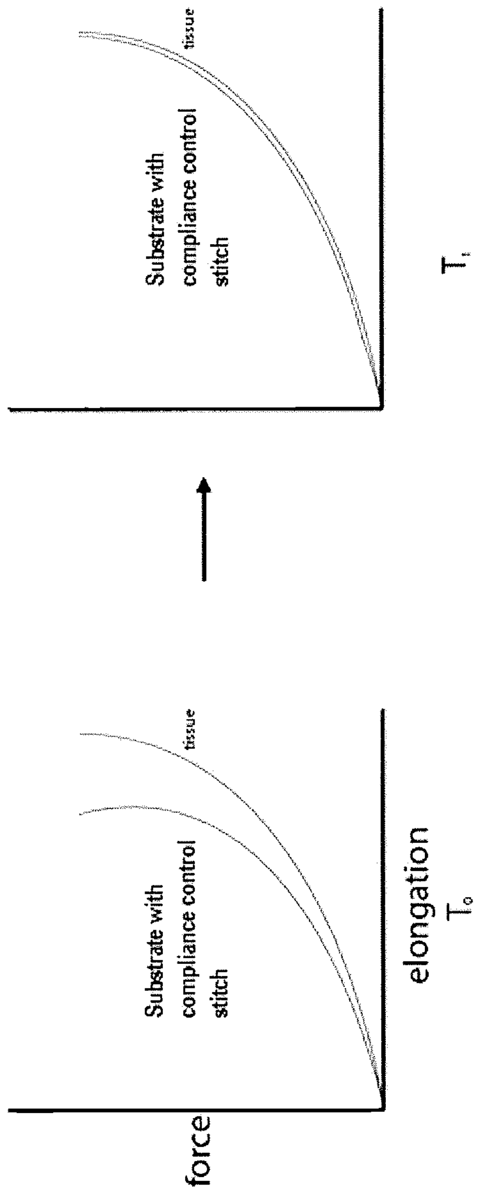
FIG. 9B shows a graphical illustration of compliance control. In this figure, a biotextile substrate having compliance control stitching has the base tensile properties (elongation as a function of force) shown at time 0 (T0), which are stiffer than the tissue into which the substrate is implanted. Over time (T1), the engineered stretch properties of the substrate have relaxed to match the compliance characteristics of the tissue.

In order to allow the substrate to relax as the natural tissue takes hold and begins to bear more of the load and movement forces, as well as to mitigate against premature weakening or failure of the substrate, compliance control may be asserted in a time-dependent manner (e.g., FIG. 9B). Time-dependent compliance control may comprise stiffening of the substrate material over time, or may comprise allowing more stretch capacity and flexibility of the substrate material over time. Time-dependent compliance control may comprise the use of compliance control stitching patterns as described herein, with the thread or yarn used to create each compliance control stitch pattern being bio-resorbable by a desired period of time.

Thus, a substrate may comprise one, or more than one compliance control stitching pattern, with each pattern comprising a thread or yarn that is resorbed at a different rate of time and, in some aspects, at least one thread or yarn that does not resorb. Thu, though one or more compliance control stitch patterns in the substrate are resorbed, at least one compliance control stitch pattern remains on a substantially permanent basis. In some aspects, the compliance control stitching patterns may be overlaid, or in different directions or orientations, or exert different degrees of compliance control. A substrate may comprise two, three, four, five, six, or more compliance control stitching patterns.

In some aspects, an implanted substrate comprises one compliance control stitch pattern. Following implantation in the body, a period of time elapses during which the substrate is substantially resorbed and, preferably, replaced by the body's natural tissue, leaving behind the stitch pattern, which serves as a support to repaired, reconstructed, or reconstituted natural tissue. Biotextile substrates are preferred examples of substrates that are resorbed. The remaining stitch pattern may thus be permanent within the body. By remaining in the body, the compliance control stitch pattern may serve to resist tearing, damage to, or other compromise to the new tissue as movement and load forces are applied to the new tissue. For example, the remaining compliance control stitch pattern may function as a backstop to prevent future herniation, degeneration, or damage at the site of the repair or reconstruction.

In some aspects, an implanted substrate material comprises one compliance control stitch pattern. Following implantation in the body, a period of time elapses during which the compliance control stitch pattern is substantially resorbed, leaving behind the substrate, which serves as a support to repaired, reconstructed, or reconstituted natural tissue. The remaining substrate may thus be permanent within the body. Thus, resorbable polymers are preferred to create the compliance control stitch pattern in a polymeric medical textile. During the period of time when the compliance control stitch pattern is present, the implanted substrate may be stronger and stiffer (e.g., less compliant) relative to the implanted substrate after the compliance control stitch pattern is resorbed, as the compliance control stitch pattern may bear the movement and load forces within the patient's body. Thus, time-dependent compliance control may involve enhancing compliance over time, as the stitch pattern is resorbed by the body.

In some aspects, an implanted substrate material comprises two or more compliance control stitch patterns. Following implantation in the body, a first period of time elapses during which a first compliance control stitch pattern is substantially resorbed, leaving behind the substrate material and the extant (second, third, etc.) compliance control stitch patterns. Subsequently, a second period of time elapses during which a second compliance control stitch pattern is substantially resorbed, leaving behind the substrate material and, if present, the extant compliance control stitch patterns. In some aspects, a third period of time elapses, during which the substrate is substantially resorbed, leaving behind the extant compliance control stitch patterns. A remaining compliance control stitch pattern may function as a backstop to prevent future herniation, degeneration, or damage at the site of the repair or reconstruction.

As each compliance control stitch pattern is substantially resorbed, the compliance of the implanted substrate may either enhance (the capacity of the substrate to stretch increases) or diminish (the capacity of the substrate to stretch decreases). Thus, for example, each subsequent compliance control stitch pattern may be intended to constrain the stretch capacity of the substrate material, or may be intended to increase the stretch capacity of the substrate material. Increasing or decreasing the stretch capacity of the substrate may comprise one or more of the compliance control factors described or exemplified herein.

In some aspects, time-dependent compliance control includes directional compliance control. Thus, for example, following implantation, the compliance of the substrate may be permitted in one or more directions, but constrained in other directions. After a first period of time elapses, a first compliance control stitch pattern has been resorbed, leaving behind the substrate material and the extant (second, third, etc.) compliance control stitch patterns. Once the first compliance control stitch pattern is resorbed, the directional control that stitch pattern exerted is absent, such that the directional control exerted by the remaining compliance control stitch patterns takes over (e.g., the direction of compliance control from the second stitch pattern is different from the direction of compliance control from the resorbed first stitch pattern, etc.).

For time-dependent compliance control, including directional time-dependent compliance control, the period of time (for resorption of a given stitch pattern and/or the substrate) may be any suitable period of time, which may depend, for example, on the typical time for natural reconstitution of the body's tissue at the repair or reconstruction site, or particular characteristics, condition, or needs of the patient. The period of time may be measured in days, weeks, months, or years. The period of time may be from about 2 weeks to about ten weeks, from about 4 weeks to about 10 weeks, or from about 4 weeks to about 8 weeks. The period of time may be from about 2 months to about six months, from about 2 months to about 12 months, from about 2 months to about 18 months, from about 2 months to about 24 months, from about 6 months to about 9 months, from about 6 months to about 12 months, from about 6 months to about 18 months, from about 6 months to about 24 months, from about 3 months to about 9 months, from about 4 months to about 8 months, from about 4 months to about 12 months, from about 12 months to about 60 months, from about 12 months to about 48 months, from about 12 months to about 36 months, from about 12 months to about 24 months, or from about 12 months to about 18 months. The period of time may be controlled, for example, by the choice of materials such that the substrate or thread or yarn may be selected based on the known resorption characteristics of the material out of which the substrate, thread, or yarn was made.

In some aspects, an implanted substrate material comprises one or more compliance control stitch patterns. Following implantation in the body, neither the substrate material nor the one or more compliance control stitch patterns are substantially resorbed. The compliance control stitch pattern may function as a backstop to prevent future herniation, degeneration, or damage at the site of the repair or reconstruction, for example, in the event of failure of the substrate.

Substrates comprising compliance control stitch patterns may be used therapeutically, for example, by implanting such substrates in the body of a subject in need thereof. The subject may be any animal, such as a laboratory or companion or farm animal. The subject is preferably a human being. Substrates are preferably surgically implanted. Implantation may be as part of any tissue repair or tissue reconstruction procedure. Thus, methods for treating a subject in need of hernia repair or soft tissue repair or regeneration may comprise implanting a substrate comprising one or more compliance control stitch patterns in at the site of hernia repair or at the site of soft tissue repair, tissue reconstruction, or tissue regeneration. The substrate and compliance control stitch pattern attendant to this method may be any substrate and any compliance control stitch pattern described or exemplified herein.

Substrates comprising one or more compliance control stitch patterns may be used in the treatment or repair of a hernia. Substrates comprising one or more compliance control stitch patterns may be used in the reconstruction of damaged or diseased tissue, including breast reconstruction. The substrate and compliance control stitch pattern attendant to such uses may be any substrate and any compliance control stitch pattern described or exemplified herein.

The following examples are provided to describe the invention in greater detail. They are intended to illustrate, not to limit, the invention.

Example 1

Uniaxial Tension Test

Figure 10:
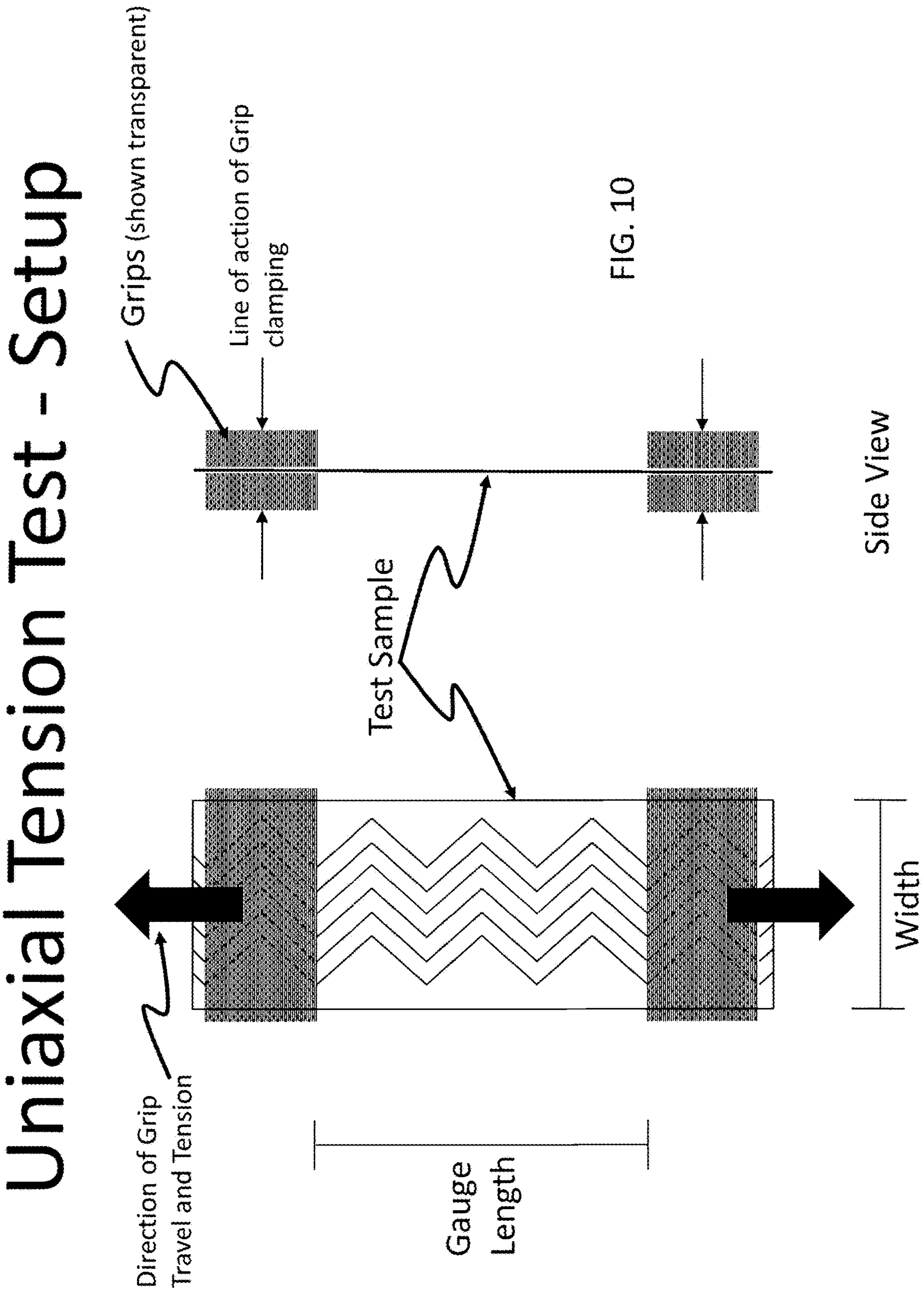
FIG. 10 shows a representation of a uniaxial tension test device. The left side of the figure shows a top perspective of the test device set-up, with a substrate (the rectangle/"test sample") having an angled compliance control stitch pattern (angled lines) placed in grips and subject to pulling tension in the direction of the arrows. The right side of the figure shows a side perspective of the set up.

Uniaxial tensile testing was performed using an Instron 3345 Universal Testing Machine. Prior to testing, the Instron Universal Testing Machine was set up using a 500 N load cell and a set of pneumatic side action grips. The two pneumatic side action grips were positioned such that the distance between their serrated jaw faces was equal to 75 mm for the start of every test. Test specimens were die cut into 6×14 cm strips and clamped into two sets of serrated jaw faces on the pneumatic side action grips using 20 psi of pressure. Pieces of rubber were used to prevent test specimens from slipping out of the pneumatic side action grips where appropriate. A representation of the test set-up is shown in FIG. 10.

Once test specimens were adequately secured, testing began. At a rate of 305 mm/min, the crosshead of the Universal Testing Machine displaced upward, creating tension in each test specimen, which was fixed to the bottom pneumatic side action grips. The crosshead displaced until the test specimen was no longer under significant tension (at least 50% of previous peak load), or broke.

Compliance strain was determined by calculating the strain at a predetermined load value. In this instance, a load value of 16 N/cm was used as it is a standard load value used in hernia mesh literature. 16 N/cm refers to 16 Newtons of load per centimeter test specimen width. In this testing application, test specimens measured 6 centimeters in width.

$$16\frac{\text{N}}{\text{cm}}*6\text{ cm}=96\text{ N}$$

The displacement of the test specimen at the first instance of 96 N is recorded and becomes the variable d. Compliance strain was calculated at this point using the following formula:

$$\text{Compliance strain}=\frac{d}{d_0},\text{ expressed as a percent where}$$

$$d=\text{displacement at first instance of 96 N}$$

$$d_0=\text{test gauge length}$$

For all tests included herein, the gauge length was equal to 75 mm. The results of these tests are shown in FIG. 11A and FIG. 11B.

The disclosure is not limited to the embodiments described and exemplified above, but is capable of variation and modification within the scope of the appended claims.

What is claimed is:

1. An implant for repairing or reconstructing soft tissue, the implant comprising:

a substrate comprising a plurality of layers, wherein each layer comprises a biotextile or a medical textile; and a triaxial compliance control stitch pattern sewn or embroidered into the substrate, wherein the triaxial compliance control stitch pattern comprises a first compliance control stitch pattern, a second compliance control stitch pattern and a third compliance control stitch pattern that overlie each other to form the triaxial compliance control stitch pattern, wherein the first, second and third compliance control stitch patterns share vertices.

2. The implant of claim 1, wherein the triaxial compliance control stitch pattern increases a peak compliance strain of the substrate so that the peak compliance strain of the implant at 16 N/cm is between 10% and 30%.

3. The implant of claim 1, wherein the first, second and third compliance control stitch patterns are the same.

4. The implant of claim 1, wherein the first compliance control stitch pattern is different than the second and/or third compliance control stitch patterns.

5. The implant of claim 1, wherein the first compliance control stitch pattern is sewn into the second compliance control stitch pattern.

6. The implant of claim 1, wherein at least one of the first, second and third compliance control stitch patterns have a zig-zag pattern comprising repeating vertices.

7. The implant of claim 1, wherein each of the first and second compliance control stitch patterns interlock at vertices.

8. The implant of claim 1, wherein each of the first, second and third compliance control stitch patterns comprise repeating vertices, wherein the vertices of the first compliance control stitch pattern are the same angles as the vertices of the second compliance control stitch pattern.

9. The implant of claim 1, wherein the first compliance control stitch pattern is oriented in a different direction than the second compliance control stitch pattern and the third compliance control stitch pattern.

10. The implant of claim 1, wherein at least one of the first, second and third compliance control stitch patterns comprises a plurality of straight lines oriented along one or more axes of the substrate.

11. The implant of claim 1, wherein at least one of the first, second and third compliance control stitch patterns are resorbable by a human body so that a peak compliance strain of the implant changes over time while implanted in a subject.

12. An implant for repairing or reconstructing soft tissue, the implant comprising:

a substrate comprising a plurality of layers comprising a biotextile, a medical textile, or both a biotextile and a medical textile; and a first compliance control stitch pattern, a second compliance control stitch pattern, and a third compliance control stitch pattern sewn or embroidered into the substrate, wherein the first, second and third compliance control stitch patterns form a triaxial pattern so that a peak compliance strain of the implant at 16 N/cm is between 10% and 30%, wherein the first, second and third compliance control stitch patterns share vertices.

13. The implant of claim 12, wherein the triaxial pattern has a high density in which the first, second and third compliance control stitch patterns comprise about 0.5 mm to about 12 mm per stitch.

14. The implant of claim 12, wherein the first, second and third compliance control stitch patterns each comprise a plurality of straight lines oriented along one or more axes of the substrate.

15. The implant of claim 12, wherein at least one of the first, second and third compliance control stitch patterns comprises a grid pattern.

16. An implant for repairing or reconstructing soft tissue, the implant comprising:

a substrate comprising a plurality of layers, wherein each layer comprises a biotextile or a medical textile; and a triaxial compliance control stitch pattern sewn or embroidered into the substrate, wherein the triaxial compliance control stitch pattern comprises a first compliance control stitch pattern, a second compliance control stitch pattern and a third compliance control stitch pattern that overlie each other to form the triaxial compliance control stitch pattern, wherein the first, second and third compliance control stitch patterns comprise about 0.5 mm to about 12 mm per stitch, wherein the first, second and third compliance control stitch patterns share vertices.

* * * * *